(12) United States Patent
Lefeber

(10) Patent No.: US 10,080,673 B2
(45) Date of Patent: Sep. 25, 2018

(54) ARTICULATED PROSTHESIS OR ORTHOSIS JOINT

(75) Inventor: Dirk Lefeber, Puurs (BE)

(73) Assignee: Vrije Universiteit Brussel, Brussels (BE)

( * ) Notice: Subject to any disclaimer, the term of this patent is extended or adjusted under 35 U.S.C. 154(b) by 170 days.

(21) Appl. No.: 13/497,371

(22) PCT Filed: Sep. 21, 2010

(86) PCT No.: PCT/IB2010/054263
§ 371 (c)(1),
(2), (4) Date: Mar. 21, 2012

(87) PCT Pub. No.: WO2011/033492
PCT Pub. Date: Mar. 24, 2011

(65) Prior Publication Data
US 2012/0185052 A1  Jul. 19, 2012

(30) Foreign Application Priority Data

Sep. 21, 2009  (WO) .................. PCT/IB2009/054137

(51) Int. Cl.
| | | |
|---|---|---|
| A61F 2/64 | (2006.01) |
| A61F 2/66 | (2006.01) |
| A61F 2/50 | (2006.01) |
| A61F 2/68 | (2006.01) |
| A61F 2/74 | (2006.01) |

(52) U.S. Cl.
CPC .............. *A61F 2/6607* (2013.01); *A61F 2/68* (2013.01); *A61F 2002/503* (2013.01); *A61F 2002/5007* (2013.01); *A61F 2002/5009* (2013.01); *A61F 2002/5018* (2013.01); *A61F 2002/5038* (2013.01); *A61F 2002/5039* (2013.01); *A61F 2002/5073* (2013.01); *A61F 2002/5075* (2013.01); *A61F 2002/5093* (2013.01); *A61F 2002/6657* (2013.01);
(Continued)

(58) Field of Classification Search
USPC ....................................... 623/50–52
See application file for complete search history.

(56) References Cited

U.S. PATENT DOCUMENTS

| 3,551,914 A | 1/1971 | Woodall |
| 5,246,465 A * | 9/1993 | Rincoe et al. .................. 623/39 |

(Continued)

FOREIGN PATENT DOCUMENTS

| WO | 9853769 A1 | 12/1998 |
| WO | 2005097009 A1 | 10/2005 |
| WO | 2006112774 A1 | 10/2006 |

*Primary Examiner* — Jacqueline Woznicki
(74) *Attorney, Agent, or Firm* — Laurence A. Greenberg; Werner H. Stemer; Ralph E. Locher

(57) ABSTRACT

A prosthesis or orthosis has a first body and a second body rotatable relative to one another, a passive mechanical converting mechanism with a third body arranged movably with respect to the first body, and an elastic element arranged between the third and the second body. The mechanical converting mechanism is configured for converting an angular change between the first body and the second body into a change of load on the elastic element. There is further provided a ratio adapting device interacting with the converting mechanism and configured for modifying the conversion ratio by which the change of load on the elastic element is performed.

14 Claims, 16 Drawing Sheets

(52) U.S. Cl.
    CPC ........... *A61F 2002/6664* (2013.01); *A61F 2002/6671* (2013.01); *A61F 2002/6692* (2013.01); *A61F 2002/741* (2013.01)

(56) References Cited

U.S. PATENT DOCUMENTS

| | | | |
|---|---|---|---|
| 5,314,499 A | 5/1994 | Collier, Jr. | |
| 2004/0243253 A1* | 12/2004 | Cool ................. | A61F 2/60 623/52 |
| 2007/0061016 A1* | 3/2007 | Kuo .................. | A61F 2/66 623/24 |
| 2008/0269912 A1* | 10/2008 | Gobbers et al. ........ | 623/27 |
| 2009/0030530 A1* | 1/2009 | Martin ................ | 623/53 |
| 2009/0192619 A1* | 7/2009 | Martin et al. .......... | 623/18.11 |
| 2009/0299480 A1* | 12/2009 | Gilbert .............. | A61F 2/582 623/18.11 |
| 2009/0299489 A1 | 12/2009 | Gramnaes | |
| 2010/0030343 A1* | 2/2010 | Hansen et al. ......... | 623/47 |
| 2010/0185301 A1* | 7/2010 | Hansen ............. | A61F 2/6607 623/47 |
| 2012/0016493 A1* | 1/2012 | Hansen et al. ......... | 623/50 |

\* cited by examiner

ARTICULATED PROSTHESIS OR ORTHOSIS JOINT

BACKGROUND OF THE INVENTION

Field of the Invention

The present invention relates to a prosthesis or orthosis.

Such a prosthesis or orthosis can for example be used for replacing or supporting an ankle joint or any other joint in a human body or can even be used as a joint in a robot.

Many types of prostheses or orthoses exist, which can be subdivided into some categories based for example on the following criteria.

A first criterion is to look if the prosthesis is stiff or rather compliant.

The existing prostheses and orthosis which are stiff have the disadvantage of being disappreciated by their users, since their stiff behavior reduces very much the comfort during walking.

A second criterion is to verify if the prosthesis or orthosis is provided with active driving means, such as for example an electrically driven actuator, or, if it is on the contrary only equipped with passive elements, such as for example a torsion spring, a leaf spring, an elastic beam, a damper, a hydraulic system, etc . . . .

The existing prostheses and orthoses of the active type provide often a relative good comfort to the user.

Nevertheless, their active driving means require an energy supply, for example in the form of a battery, which makes the prosthesis or orthosis often rather heavy.

Other disadvantages of this active type of prostheses or orthoses are their limited operation time due to battery discharging and the high costs related to their production.

In order to avoid said draw-backs of the afore-mentioned prostheses or orthoses of the stiff type and/or active type, the present invention is related to a prosthesis or orthosis which is of the compliant type having in first instance only passive driving elements.

More in particular, the present invention relates to a prosthesis or orthosis comprising a first body, a second body and an articulated joint between said bodies, the articulated joint allowing the rotation of said bodies with respect to one another.

Hereby, an elastic element is mounted between said bodies which is intended for exerting a moment force on the bodies in such a way that the moment force tends to bring the bodies back into an equilibrium position relative to one another in which position the spring means do not exert said moment force between the bodies.

Such prostheses or orthoses of the compliant and passive type already exist, but their major disadvantage is that their mechanical behavior is very much differing from the behavior of a human body joint, in particular from the behavior of a human ankle joint or knee joint.

In the existing prostheses or orthoses of the compliant, passive type, during a change in angular position between the first body and the second body out of the equilibrium position, energy is stored in the elastic element.

When the first body and the second body are brought back into their original angular positions, said energy stored in the elastic element is simply released again.

In a human body ankle joint the behavior is completely different.

Actually, the problem with said existing prostheses or orthoses of the passive, compliant type is that the stiffness of the elastic element is remaining fixed in all circumstances, whereas in a real human body ankle the stiffness of the connection changes during the normal gait cycle, as will be explained further in the text.

What's more, in the existing prostheses or orthoses of the passive, compliant type, also the equilibrium position defined by an angular position between the bodies, in which position the elastic element is not exerting any moment force on the bodies, is remaining unmodified during forward and backward rotation of the bodies relatively to one another.

On the contrary, in a real, human body ankle said equilibrium position seems to change during the gait cycle.

For these reasons, the energy stored in the elastic element of said existing prostheses is released at another moment during the gait cycle and at a faster rate and thus over a shorter angle range, as compared to the functioning of a human body ankle joint.

As a consequence, during the push-off phase of the gait cycle, i.e. when the toe is pushed off from the ground, the so-called plantar flexion phase, the existing prostheses release there stored energy in a too short angle range and in a somewhat intense or unbalanced manner. After the members have rotated the said shorter angle range, no energy is kept available for further plantar flexion so that less energy is available for accelerating the human body.

This is an important reason for the discomfort felt by a user of an aforementioned existing prosthesis or orthosis of the passive type.

BRIEF SUMMARY OF THE INVENTION

The present invention aims at a prosthesis or orthosis which does not show one or more of the above disadvantages and possibly also other disadvantages.

In particular, it is an aim of the present invention to provide a prosthesis or orthosis having a mechanical behaviour which is closer to the mechanical behavior of a human body joint than in the existing prostheses and ortheses and which is more energy efficient than the existing prostheses and ortheses.

To this aim, the invention relates to a prosthesis or orthosis comprising a first body, a second body and an articulated joint between said bodies, the articulated joint allowing the rotation of said bodies with respect to one another, an elastic element mounted between the bodies, the prosthesis or orthosis being equipped with a passive mechanical converting mechanism which comprises a third body arranged movably with respect to the first body, the elastic element more particularly arranged between the third and the second body, the mechanical converting mechanism arranged for converting an angular change between the first body and the second body into a change of load on the elastic element, the prosthesis or orthosis further comprising ratio adapting means interacting with the mechanical converting mechanism arranged for modifying the conversion ratio by which the change of load on the elastic element is performed.

A first important characteristic of a prosthesis or orthosis according to the present invention, is that an angular change between the first body and the second body is not transferred directly to the elastic element, but through a passive mechanical converting mechanism.

In that manner, an angular change between the first body and the second body, which will be indicated further in the text as the input angular change, can be amplified or weakened by the passive converting mechanism with a certain ratio before it is supplied to the elastic element and this without the need for an additional active power supply.

The conversion results in a change at the output of the converting mechanism, preferably in an output angular change which is applied between the second body and the third body in order to stretch or compress the elastic element mounted between said second body and third body.

The conversion ratio of the converting mechanism is defined as being the amplitude of the change at the output of the converting mechanism divided by the input angular change between the first body and the second body at the input of the converting mechanism.

Hereby, the change at the output of the converting mechanism is preferably said output angular change between the third and second body, but not necessarily.

Furthermore, it is assumed that in first instance the stiffness of the elastic element is remaining unmodified.

The foregoing means that the same input angular change results in a high output change of load on the elastic element if the conversion ratio of the converting mechanism is high, whereas the resulting output change of load on the elastic element is small when the conversion ratio is small.

So, the change of load on the elastic element felt by a user when rotating the first and the second body with respect to one another is function of the conversion ratio of the converting mechanism.

The combination of the elastic element with the converting mechanism can therefore be considered as being an elastic system mounted between the first and the second body, which elastic system has a stiffness that can be set independently from the stiffness of its elastic element by choosing the right conversion ratio for its converting mechanism.

A second important characteristic of a prosthesis or orthosis according to the present invention is that it is provided with ratio adapting means which interact with the aforementioned converting mechanism and by which the conversion ratio performed by the converting mechanism can be set.

From the foregoing it is understood that with a prosthesis or an orthosis in accordance with the present invention, the stiffness of the joint, which is formed by the combination of the elastic element and the converting mechanism, can be changed during the gait cycle, which is a requirement to be fulfilled for having a human body like joint behavior.

Indeed, with the ratio adapting means the conversion ratio of the converting mechanism can be modified and as a consequence a different stiffness of the joint is obtained.

Hereby, it is important to notice that the mechanical converting mechanism is of the passive type, so that apart from the energy supplied by the user when rotating the first and second body with respect to one another, no additional energy is required, for example in the form of active actuators or the like, for modifying the stiffness of the joint.

Another consequence of having a converting mechanism, provided with a ratio adapting means by which its conversion ratio can be modified, is that by changing said conversion ratio during the gait cycle, the angular position in which the first body and second body are in an equilibrium position is not necessarily remaining fixed.

Indeed, an equilibrium position between the first body and the second body is an angular position in which the elastic element is not exerting any moment force on said bodies.

So, assume the angular position between the first body and the second body is changed out of such an equilibrium position, while the converting mechanism is applying a first conversion ratio, this would result in a first change of load on the elastic element.

When the first body and the second body are then again brought back to their initial angular position, while the converting mechanism is applying a second conversion ratio, this will result in a second change of load on the elastic element which is not simply the opposite of the first change of load on the elastic element.

Therefore, when the first body and the second body are again in their initial angular position, this is generally not any more an angular position in which the elastic element is not exerting any moment force, so that the initial angular position is not any more an equilibrium position.

An interesting case is the one in which the conversion ratio is set to be zero by the ratio adapting means.

In that case no matter what input angular change is applied, there will be no change at the output of the converting mechanism and thus neither a change of load on the elastic element will be realized, so that the equilibrium position is set freely.

From the foregoing, it is clear that with a prosthesis or orthosis according to the present invention the stiffness of the joint as well as the equilibrium position of the joint can be set easily, without any need for additional external energy.

This means that such a prosthesis or orthosis is very suitable for imitating the behavior of human joints, for example the of the human ankle joint.

According to a preferred embodiment of a prosthesis or orthosis in accordance with the present invention, the first body and the second body are coupled at one end to each other by means of the articulated joint, the remaining part of the bodies extending substantially in only one sense away from the articulated joint.

In that way the physical configuration of the prosthesis or orthosis resembles to the human body joints or even the joints in robots.

Indeed, for example in a human ankle joint the foot and the lower leg are coupled at the ankle with their one end, while the rest of the foot and the lower leg are extending substantially only in one direction away from the ankle joint.

The same physical configuration exists for example in a knee or an elbow.

As an alternative, a prosthesis or an orthosis in accordance with the present invention can be provided with coupling means for connecting such type of bodies to it, which extend substantially only in one sense.

According to another preferred embodiment of a prosthesis or orthosis in accordance with the present invention the ratio adapting means are such that during a relative rotation of the first body and the second body in a first sense, the aforementioned conversion ratio is different from the ratio performed during a relative rotation of the first body and the second body in the opposite sense.

Such a prosthesis or orthosis according to said embodiment is particularly interesting, since in that way the stiffness of the joint is different when the first body and the second body are rotated in a first sense, as compared to the stiffness when the rotation is in said opposite sense.

A similar characteristic is present in the human body ankle joint, since during the gait cycle the stiffness of the human body ankle joint appears to be different when the foot is rotated towards the lower leg, i.e. during the so-called dorsal flexion, as compared to the stiffness when the foot is rotated in the opposite sense, i.e. during the so-called plantar flexion.

According to an even more preferred embodiment, the ratio adapting means in a prosthesis or orthosis according to the present invention, are such that the conversion ratio is modified to be higher during a relative rotation of the first body and the second body in a first sense corresponding to the dorsal flexion phase of the gait cycle, wherein the smallest angle between the aforementioned extending body parts is decreased, than during a relative rotation of the first body and the second body in the opposite sense corresponding to the plantar flexion phase of the gait cycle, wherein the smallest angle between said extending body parts is increased.

With this embodiment of a prosthesis or an orthosis according to the invention, the human ankle joint is even more closely imitated.

Indeed, the human ankle joint appears to have a changing stiffness during the gait cycle which is such that when the lower leg and foot are moved towards one another the stiffness is higher than in the opposite sense.

In order to realize the aforementioned converting mechanism in a justifiable and practical way, a prosthesis or an orthosis in accordance with the present invention has a mechanical converting mechanism which preferably comprises gear wheels.

Even more preferably, said mechanical converting mechanism comprises a planetary gear system with a ring wheel, a sun wheel and one or more planetary wheels mounted on planet shafts which are rotatable around their planet gear axis, which axes are positioned at fixed positions on a planet carrier, the planetary wheels intermeshing with the ring wheel as well as with the sun wheel.

Said embodiment of a prosthesis or an orthosis in accordance with the present invention can be made in a very compact and light way and is very energy efficient.

Another advantage of this embodiment is that no complicated ratio adapting means are needed for changing the conversion ratio of the converting mechanism.

Indeed, in a planetary gear system many different conversion ratios can be chosen for example just by taking the right gears for the input and the output of the converting mechanism or by blocking the rotation of some gear wheels of the planetary system to one another.

As a consequence it is sufficient for example to connect the first body, the second body and/or the third body to the right gear wheels in order to obtain the desired conversion ratio or to block certain gear wheels of the planetary system at the right moment.

Therefore, according to another preferred embodiment of a prosthesis or orthosis according to the invention the ratio adapting means consists of a locking or braking mechanism for locking and unlocking gears of the converting mechanism to one another or to the bodies.

Preferably, said locking or braking mechanism comprises at least one or more pawls or brakes.

It is clear that such ratio adapting means are very simple to put in practice in a economically justifiable manner.

Furthermore, such ratio adapting means can easily be manipulated without any complication.

With the intention of better showing the characteristics of the invention, hereafter, as an example without any restrictive character whatsoever, a preferred form of embodiment of a prosthesis according to the present invention, is described, with reference to the accompanying drawings, wherein:

DESCRIPTION OF THE INVENTION

Figure 1:
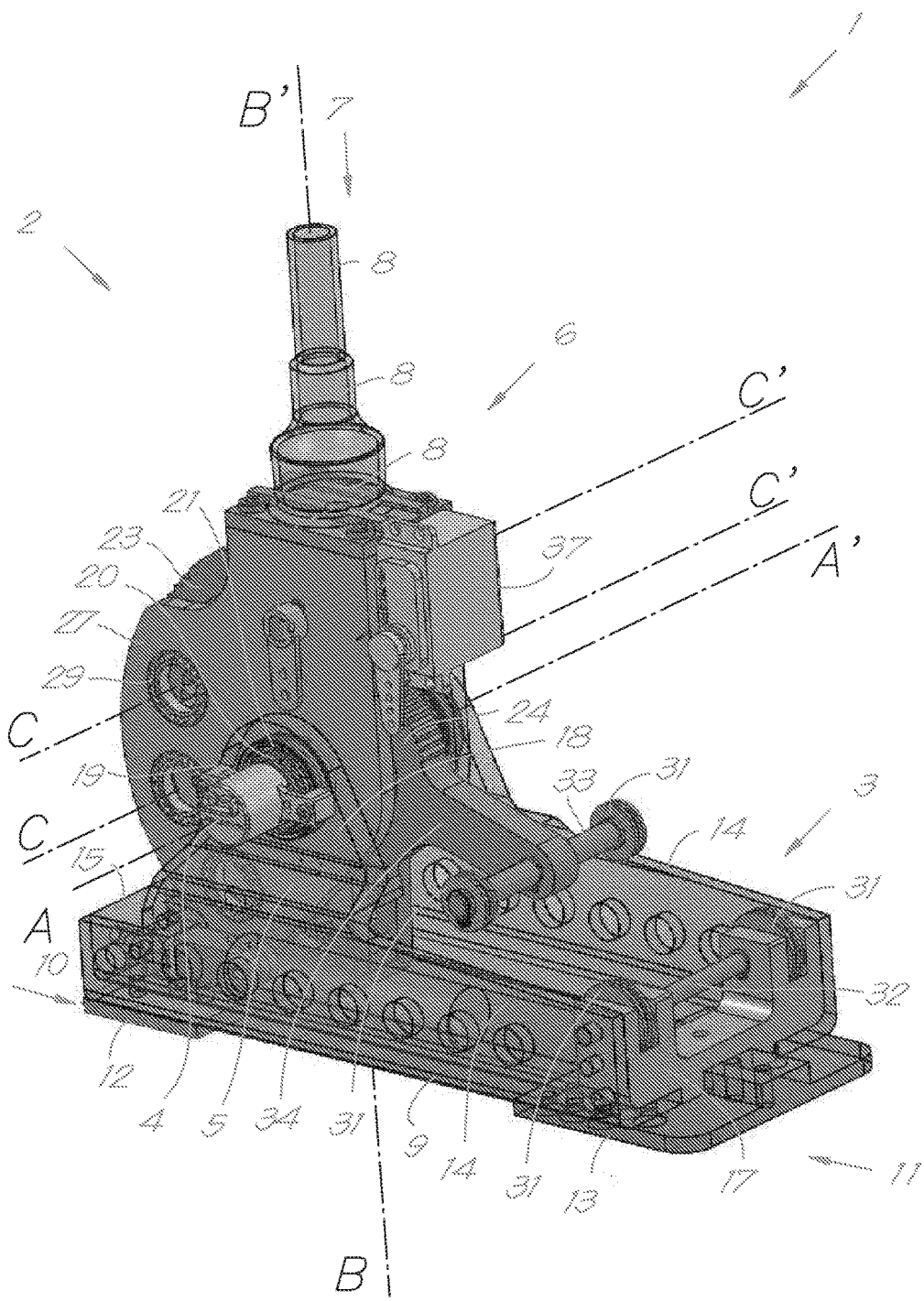
FIGS. 1 and 2 represent a preferred embodiment according to the invention, respectively in a perspective view and in a side view.
Figure 2:
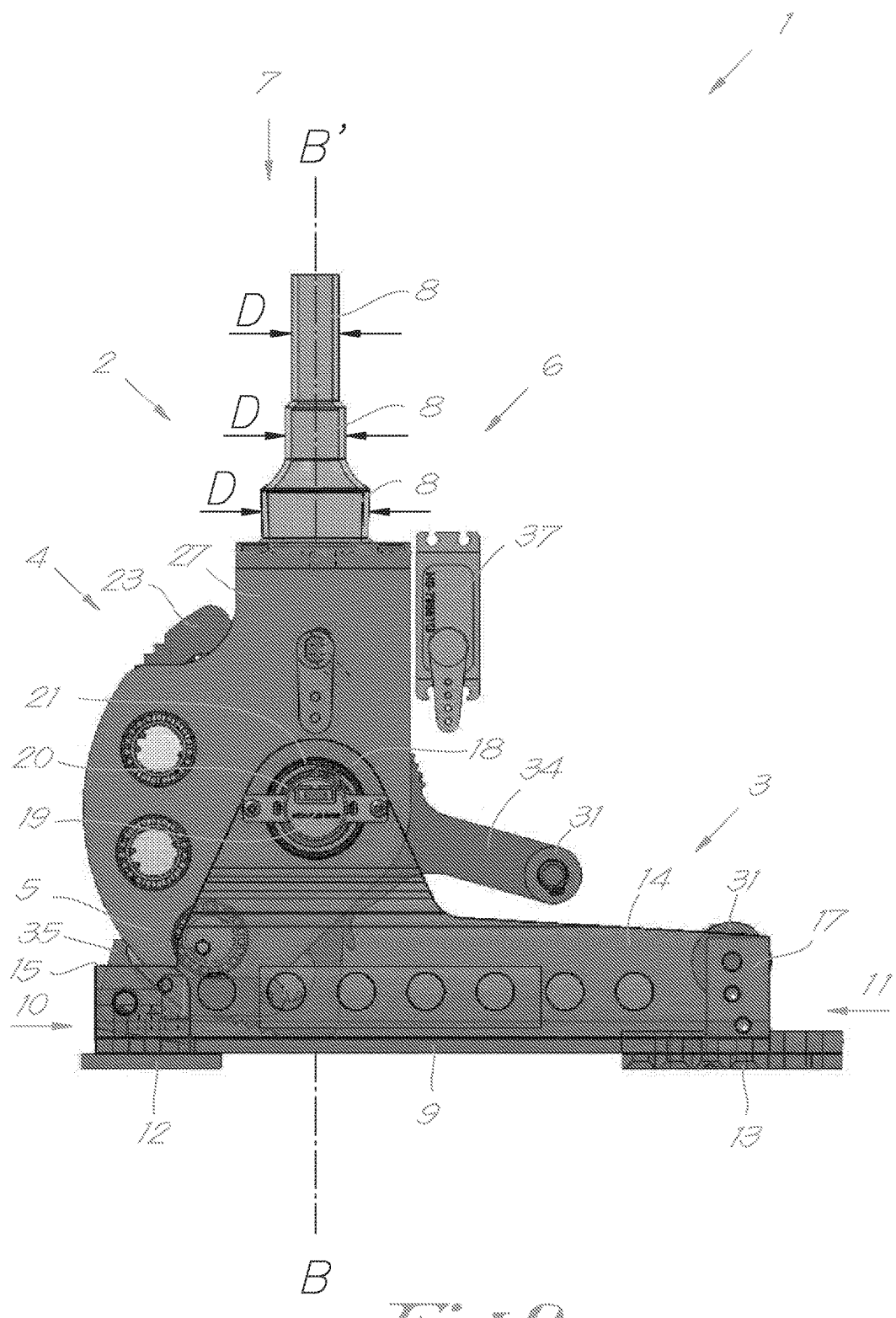
Figure 3:
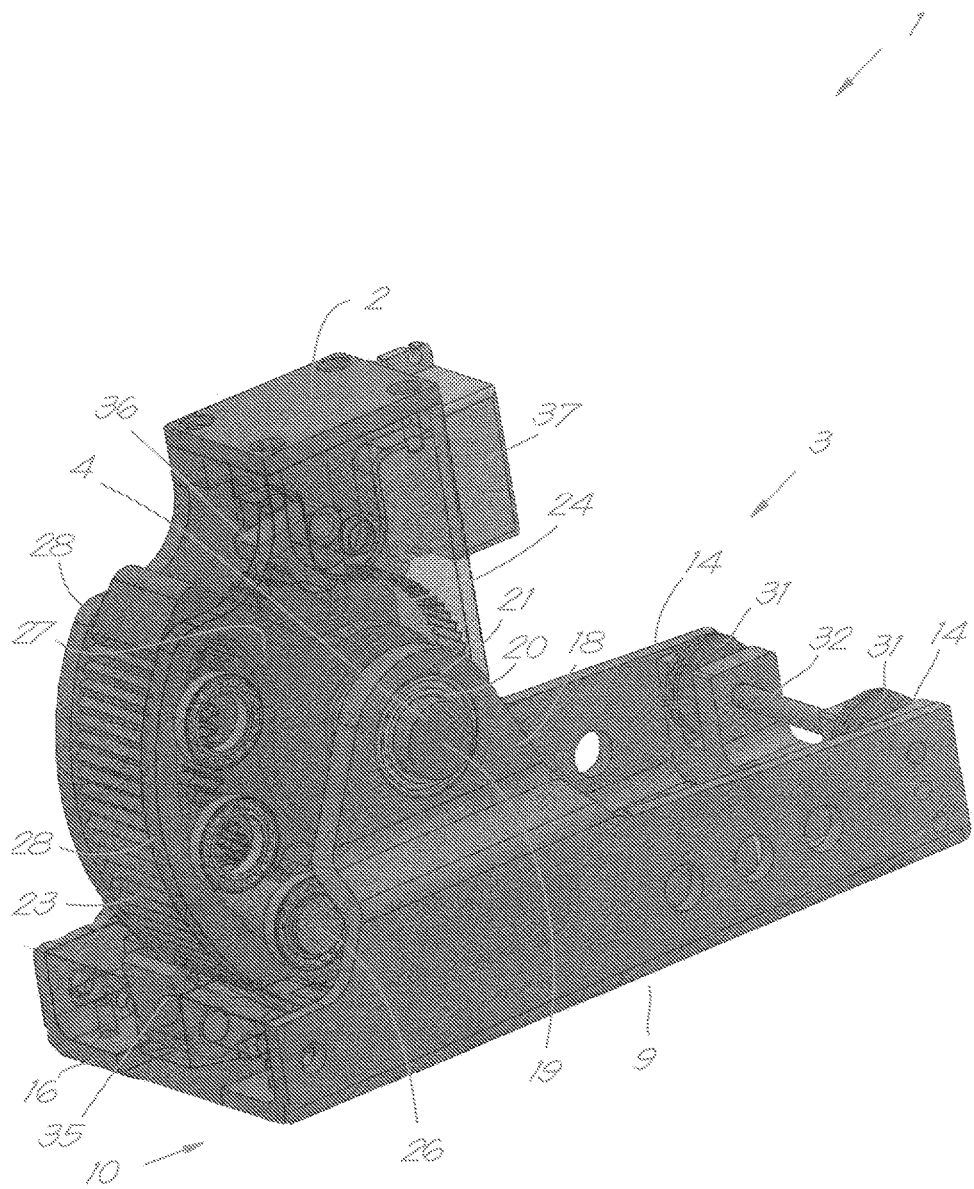
FIG. 3 represents a perspective view on a prosthesis according to the present invention, some parts being left away for better demonstrating the inside mechanism.

The prosthesis 1 according to the present invention represented in FIGS. 1, 2 and 3 is intended for replacing an ankle of a human body.

It comprises a first body 2, a second body 3 and an articulated joint 4 between said bodies 2 and 3.

The articulated joint 4 allows the rotation of the first body 2 and the second body 3 with respect to one another around an axis AA'.

In this case, the first body 2 is intended for being linked to a lower leg part of a person.

To that aim it has a more or less elongated shape which is connected with its one end 5 by means of the articulated joint 4 to the second body 3, whereas the remaining part 6 of the first body 2 is extending substantially in one sense in the direction BB', which is perpendicular to the axis AA' of the articulated joint 4.

Hereby, the far most end 7 of the remaining part 6 of the first body 2 is shaped into some tube like cylindrical sections 8, in this case three sections 8, which are aligned with said direction BB' and which have a decreasing diameter D when approaching the far most end 7.

The second body 3 is intended to fulfill the role of a foot and is for that reason more or less executed in the shape of a foot.

In particular, the second body 3 consists mainly of a flat elongated plate or sheet 9, which is more ore less rectangular and which is actually forming the sole of the foot shape.

Said plate 9 is at its both longitudinal ends 10 and 11 provided with a small support, respectively a heel support 12 and a toe support 13.

Furthermore, the sole 9 is bordered by side walls 14 extending in planes which are perpendicular to the sole 9 at both opposite longitudinal side edges of the sole 9.

The side walls 14 are connected to one another, in particular by an additional traverse side wall 15 at the heel side edge 16 and by a connecting piece 17 at the toe end 11 of the sole 9.

The side walls 14 are each near their heel end 10 provided with an ear 18, which ears 18 are parallel to one another and are offset inwardly somewhat from the side wall's 14 plane.

The end 5 of the first body 2 is introduced between said ears 18 provided on the second body 3.

The articulated joint 4 is in this case realized by a shaft 19 which is rotatably mounted on the second body 3 by means of roller bearings 20.

Hereto, the ears 18 are provided with a hole 21 in which the bearings 20 are provided.

The shaft 19 is mounted fixedly with respect to the first body 2, so that the bodies 2 and 3 are rotatable with respect to one another.

According to the invention the prosthesis 1 comprises a passive mechanical converting mechanism 22.

In the embodiment represented in the FIGS. 1 to 3, said converting mechanism 22 consists of a planetary gear system, having a ring wheel 23, a sun wheel 24 and, in this case, three planetary wheels 25 which intermesh with the ring wheel 23 as well as with the sun wheel 24, but which are not represented in the figures.

The planetary wheels 25 are mounted on planet shafts 26 (of which one example is represented in FIG. 3) and are rotatable around their planet gear axis CC', which axes CC' are positioned at fixed positions on a planet carrier 27.

In this case the planet carrier 27 is of the cage type having two side walls 28, the gears of the planetary system being positioned between said side walls 28.

The planet shafts 26 are connected fixedly to the planetary wheels 25 and are supported at their both ends in the side walls 28 of the planet carrier 27 by means of planet bearings 29.

The ring wheel 23 and the planetary carrier 27 are rotatable around a common shaft, which is in this case the articulated joint 4 forming shaft 19.

Details of the rotatable mounting of said parts of the planetary gear system around the common shaft 19 are not visible in the figures, but are known according to the present state of the art.

The sun wheel 24 is in this case mounted rotatably on said shaft 19 by means of a bearing or bearings not represented in the figures. The shaft 19 itself is mounted rotatably in the second body 3 by means of the bearings 20 and is connected fixedly to the first body 2, as explained.

Many other ways of assembling such a planetary system are also known according to the state of the art and it is clear that such other embodiments are not excluded from the present invention.

Furthermore, the prosthesis 1 is provided with means for mounting an elastic element 30 on the prosthesis 1 which is intended for exerting moment forces during rotation of the first body 2 and second body 3 around the shaft 19.

In the represented embodiment of FIGS. 1 to 3, said means consist of wheels 31 over which extension wires or the like connected to for example a helical tension spring are guided.

Neither the elastic element 30 itself, nor the said extension wires are shown in FIGS. 1 to 3.

On the one hand, a pair of said wheels 31 is mounted at both ends of a small shaft 32, which is located in the connection piece 17 at the toe end 11 of the second body 3 and which is parallel to the shaft 19 of the articulated joint 4.

On the other hand, a similar pair of wheels 31 at the same distance from one another is mounted at both ends of a small shaft 33, which is also parallel to the shaft 19.

Said small shaft 33 is extending at both sides of a lever 34 which is a part of the sun wheel 24 and which is extending in a radial direction from the centre of said sun wheel 24.

In the wordings of claim 1, the sun wheel 24 with its lever arm 34 corresponds in this embodiment to the third body 24 which is a part of the mechanical converting mechanism 22, said third body 24 arranged movably with respect to the first body 2, and the elastic element 30 more particularly arranged between the third body 24 and the second body 3.

It is further clear that the mechanical converting mechanism 22 is arranged for converting an angular change between the first body 2 and the second body 3, hereafter called the input angular change of the converting mechanism 22, into a change of load on the elastic element 30.

Hereby, the input angular change is converted into an output angular change, which is defined as the angular change between the third body 24 and the second body 3.

In the represented embodiment, there is a permanent link between the converting mechanism 22 formed by the planetary system and the first body 2, since the planet carrier 27 is permanently connected fixedly to the first body 2.

It is clear that this is just an example of how things can be done in order to obtain a prosthesis 1 having a behavior which is more resembling to a human ankle joint than in the existing prostheses.

In other embodiments, any gear wheel of the planetary system can be chosen for being connected permanently or temporarily with any one of the first body 2, the second body 3 or the third body 24.

According to still other embodiments of prostheses or orthoses in accordance with the invention any one of the first body 2, the second body 3 or the third body 24 can even be formed integrally with such a gear wheel of the planetary system.

Another important characteristic of a prosthesis 1 in accordance with the present invention is that it comprises ratio adapting means interacting with the mechanical converting mechanism 22, which ratio adapting means are arranged for modifying the conversion ratio by which the change of load on the elastic element 30 is performed.

In the represented embodiment, said ratio adapting means consist of a locking mechanism for locking and unlocking gears or parts of the converting mechanism 22 to one another or to the bodies.

In particular, the ratio adapting means comprises two pawls, respectively a first pawl 35 and a second pawl 36.

The first pawl is mounted rotatably around a shaft in the heel end 10 of the second body 3, for locking and unlocking the ring wheel 23 with respect to said second body 3.

The second pawl 36 is mounted rotatably around a shaft, which is extending between the planet carrier's side walls 28 and is positioned on top of the sun wheel 24.

Said second pawl 36 is intended for locking and unlocking the sun wheel 24 and the first body 2 to one another.

In the represented case, the locking and unlocking of said second pawl 36 is actuated by a motor or electrical actuator 37, but it is clear that the pawls do not necessary require such an actuator.

The energy required for such a manipulation is very small compared to the energy required in known prostheses or orthoses of the active type, as described in the introduction.

The most important advantage of a prosthesis 1 according the invention is that it is suitable for imitating the natural behavior of a human joint, in particular an ankle joint, as will be explained now.

Figure 4:
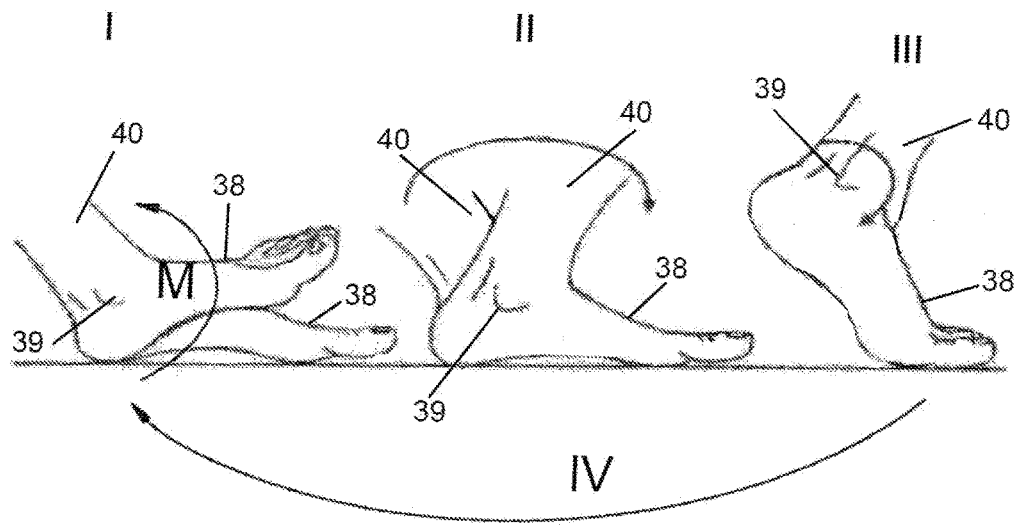
FIG. 4 illustrates the four different phases during the normal gait cycle.

First of all, it is important to understand that the normal gait cycle of a person can be divided in 4 different phases, which are illustrated in FIG. 4.

From left to right in FIG. 4, there is first phase I which is from heel strike until the foot 38 is completely on the ground. During said phase I, the ankle joint 39 is actually exerting a torque M between the foot 38 and the lower leg 40 in order to prevent the foot from falling on the ground.

Energy for exerting said torque M is supplied by the person walking and the torque M is directed in a sense that an augmentation of the angle between the foot 38 and the lower leg 40 is hindered.

The next phase II is the so-called phase of dorsal flexion II during which the lower leg 40 is brought forward, i.e. the lower leg 40 is turned towards the foot 38 which is still on the ground.

During this phase II the walking person is again supplying energy which is stored in the muscles and tendons and the body is decelerated.

The next phase III is the so-called phase of plantar flexion III or push-off phase III, during which the foot 38 is pushed-off and is leaving the ground.

In this phase III, the energy stored in the muscles during phase II is converted to motion energy by pushing off with the toe and the body is accelerated.

The last phase IV is the so-called swing phase IV of the leg 40 during which the foot 38 is rotated around the ankle 39 in order to bring the foot 38 back in its original position at heel strike.

During said swing phase IV the foot 38 is not in contact with the ground and so almost no energy is required to rotate the foot 38.

Figure 5:
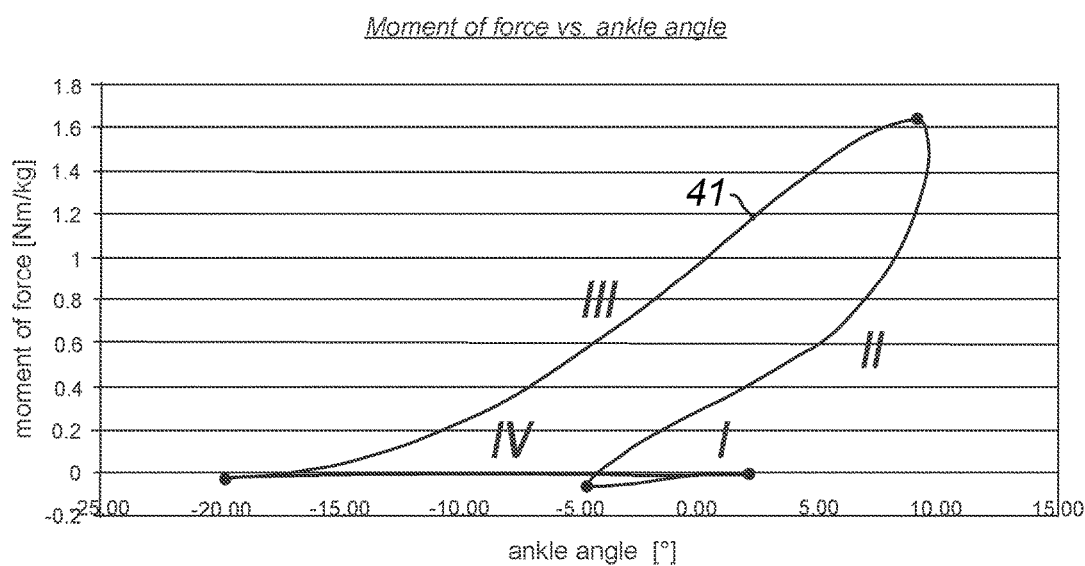
FIG. 5 represents a chart on which the moment force, experienced in the human ankle joint during the gait cycle, is set against the angular change between lower leg and the foot.

FIG. 5 is illustrating in a different way what is happening in the normal gait cycle of a human person.

In said FIG. 5 the moment force exerted by the person walking or running is plot against the angular change between the foot 38 and the lower leg 40.

The different phases I-IV during the gait cycle are indicated near the curve.

The angular position in which the foot 38 and the lower leg 40 are perpendicular to one another corresponds to the 0° position on the X-axis of the graph.

A rotation of the lower leg 40 towards the foot 38 is regarded as a positive angular change, while a rotation in the opposite sense is considered as a negative angular change.

So, phase I starts when the heel strikes on the ground, while the foot 38 is almost perpendicular to the lower leg 40. The angle between the foot 38 and the lower leg 40 is somewhat smaller than 90°. That's why the curve is starting somewhere near the 2°.

The person is supplying a small moment force in order to keep the foot 38 from flapping on the ground.

So, during phase I a small negative torque is exerted.

Said phase I is ending when the foot 38 is flat on the ground, while the lower leg 40 is still directed a bit in a forward direction, the angle between foot 38 and lower leg 40 being ±95°. This is −5° on the X-axis.

During dorsal flexion phase II the lower leg 40 is turned to the foot 38 about 15°, while energy is stored in the muscles.

Said energy is again released during the plantar flexion phase III. However, during said plantar flexion phase III the foot 38 is turned away from the lower leg 40 over a bigger angular range, i.e. there is a total angular change of about 30°.

This actually means the energy is released differently, i.e. at a slower rate, than it has been stored in the muscles.

During the swing phase IV, which is from −20° to +10° on the curve, almost no energy or force as applied. AS a consequence the curve is during said phase IV more or less collinear with the X-axis.

With the known prostheses of the passive type it is impossible to imitate such a kind of curve of the human ankle joint, since the passive elements used have only a single stiffness.

Figure 6:
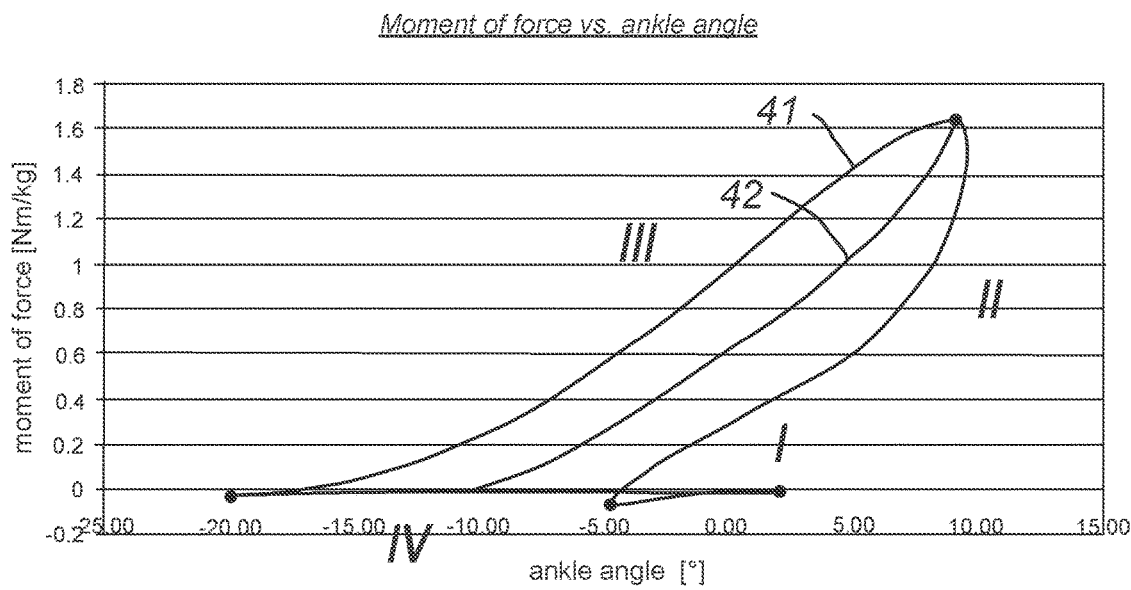
FIGS. 6 and 7 represent charts on which the same curve of FIG. 5 is repeated and is compared to the corresponding curve respectively of a known prosthesis of the passive type and a prosthesis according to the invention.

In FIG. 6 the human ankle joint curve 41 is compared to a typical curve 42 obtained with the known prostheses of the passive type having only such single stiffness.

Said curve 42 can be either linear or not, depending on the type of spring or elastic element that is used.

The energy is stored and released in the same angle range.

Known prostheses of the active type add energy to the joint, but such prostheses have the disadvantages as explained.

A particular strength of the invention relies on the fact that it is understood that no external energy has to be added to the prosthesis, but that the energy stored during the dorsal flexion phase II is spread out over a larger range during the plantar flexion phase III.

Phases II and phase III of the gait cycle can be approximated by two (straight) lines with a different slope.

When using a system which can vary the stiffness of the joint, such an approximated curve can be obtained.

In particular, when the joint is made relatively stiff during phase II, the energy is stored during a relatively small angular change between the lower leg 40 (corresponding to the first body 2) and the foot 38 (corresponding to the second body 3).

If during phase III, measures are taken to provide that the joint is less stiff as compared to phase II, the stored energy will be released over a relatively larger angular change between the lower leg 40 (corresponding to the first body 2) and the foot 38 (corresponding to the second body 3).

Figure 7:
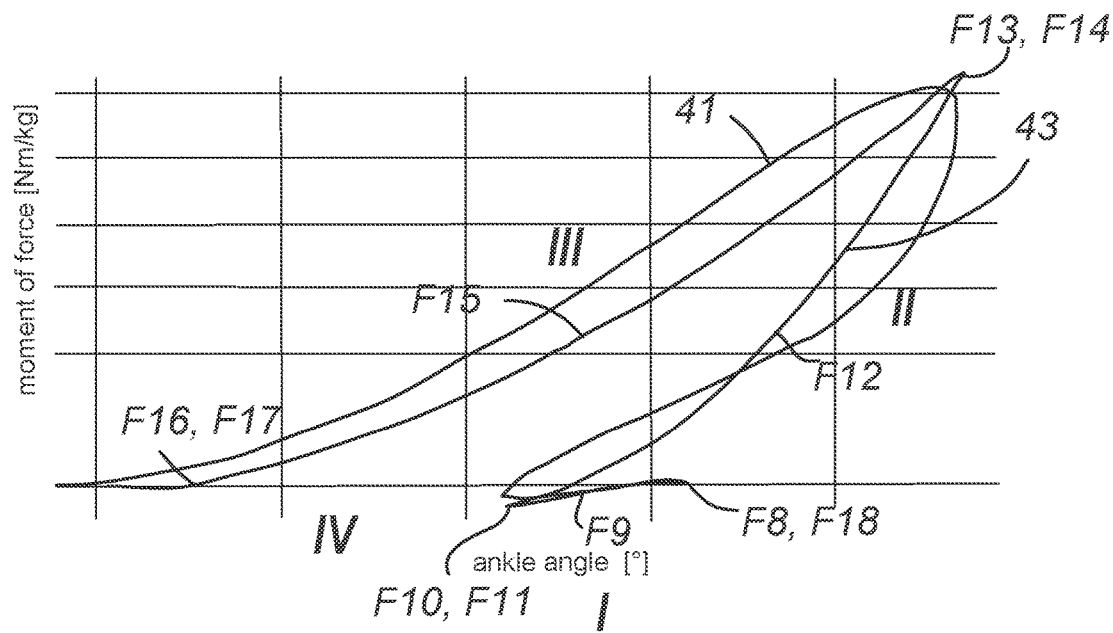

With a prosthesis 1 according to the invention this can be realized and the resulting curve 43 is illustrated in FIG. 7.

It is clear from said FIG. 7 that the curve 43 of a prosthesis according to the invention is much closer to the human ankle joint curve 41, than the curve 42 of the known prostheses of the passive type.

How in reality such a curve 43 is obtained with a prosthesis 1 according to the invention, will hereafter be explained by means of FIGS. 8 to 18, which FIGS. 8 to 18 schematically represent the position of the different parts of the converting mechanism 22, the first body 2 and the second body 3, as well as the elastic element 30, respectively during the phases of the gait cycle indicated by F8 to F18 in FIG. 7.

In the figures the second body 3 (corresponding to the foot 38) is always represented by a horizontal line.

It is clear however that said second body 3 or foot 38 is not staying horizontal during the gait cycle.

Figures 8, 9, 10:
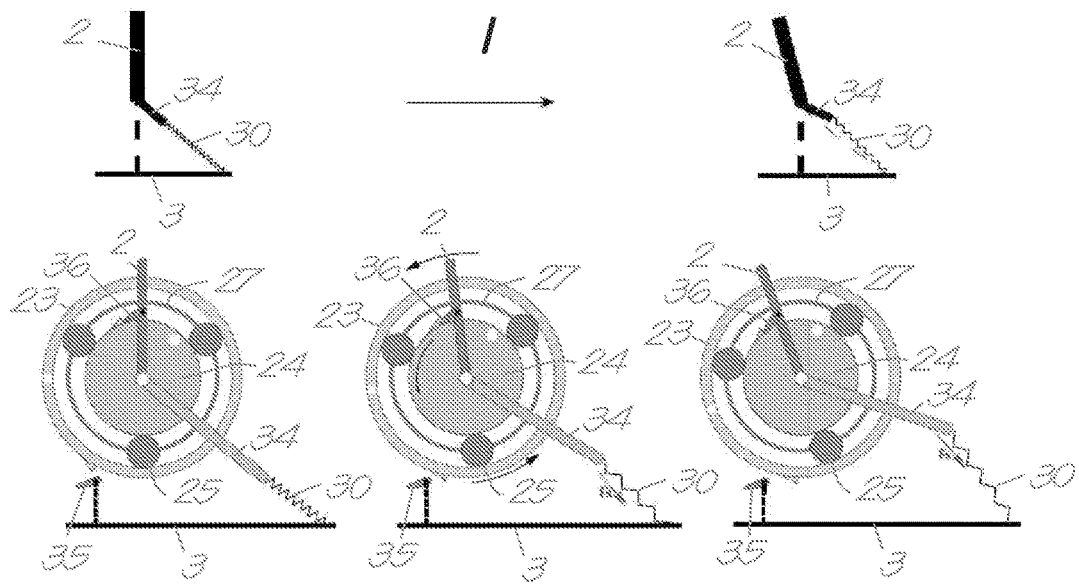
FIGS. 8 tot 10 illustrate schematically the functioning of the prosthesis of FIGS. 1 to 3 during the swing phase I of the gait cycle, respectively at the start, in the middle and at the end of said phase I.

In FIG. 8 the position at the start of the first phase I is represented.

For the sake of clearness, in the upper part of said FIG. 8, the position of the first body with respect to the second body is represented schematically.

The same is done in the other figures representing the start position and end position in the different phases I to IV.

From the lower parts of FIGS. 8 to 10, which represent phase I, it is clear that during phase I of the gait cycle the ratio adapting means, which are in this embodiment pawls 35 and 36, are such that pawl 35 is in the unlocking position allowing the free rotation of the ring wheel 23 with respect to the second body 3, whereas pawl 36 is locking the sun wheel 24 with respect to the planet carrier 27 or in other words to the first body 2.

With the pawls 35 and 36 in such a position, the gear wheels of the planetary system are not capable of turning with respect to one another, the sun wheel 24 and its lever arm 34 rotating in the same way around the shaft 19.

This means that in phase I an angular change between the first body 2 and the second body 3, which is considered as being the input of the converting mechanism 22, will result in the same angular change between the third body, represented by the lever arm 34, and the second body 3, which is considered as being the output of the converting mechanism 22.

As a consequence the converting mechanism 22 is actually applying a conversion ratio of 1 during said phase I.

The elastic element 30 is somewhat elongated during said phase I, which corresponds to a negative moment force in the curve of FIG. 7.

Figures 11, 12, 13:
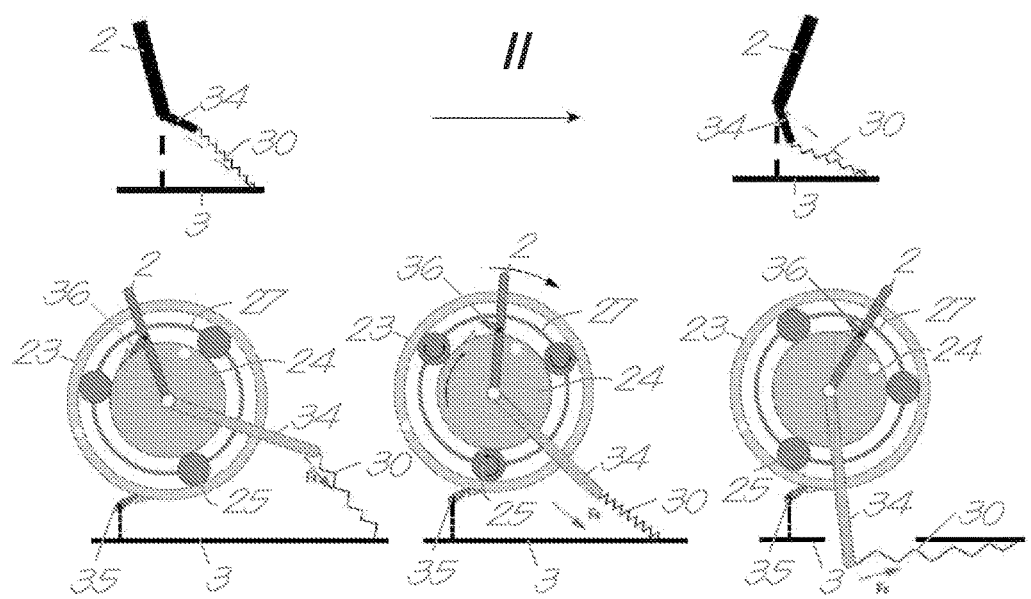
FIGS. 11 to 13, FIGS. 14 to 16 and FIGS. 17 to 19 illustrate in a similar way as in FIGS. 8 to 10 the phases II, III and IV of the gait cycle.

The next phase II of dorsal flexion, during which energy is stored in the elastic element 30, is represented in FIGS. 11 to 13.

During this phase II, the ratio adapting means are such that pawl 35 is in the locking position, i.e. the ring wheel 23 is locked with respect to the second body 3, whereas the second pawl 36 is in the unlocking position, i.e. the sun wheel 24 is allowed to rotate with respect to the planet carrier 27.

An angular change between the first body and the second body will result in this phase II in a larger angular change between the third body or lever arm 34 and the second body 3, since it is a characteristic of a planetary gear unit that a slow rotation of the planet carrier 27 is transmitted in a fast rotation of the sun wheel 24, when the ring wheel 27 is kept fixed.

So, the conversion ratio applied during said phase II is higher than during the preceding phase.

This means that a relatively small rotation at the input of the converting mechanism 22 requires a relatively big rotation at the output of the converting mechanism 22, said big rotation corresponding in this case to a big change of load on the elastic element 30.

As a consequence, the elastic behaviour of the prosthesis 1 according to the invention can be considered as being relatively stiff during this phase II.

Figures 14, 15, 16:
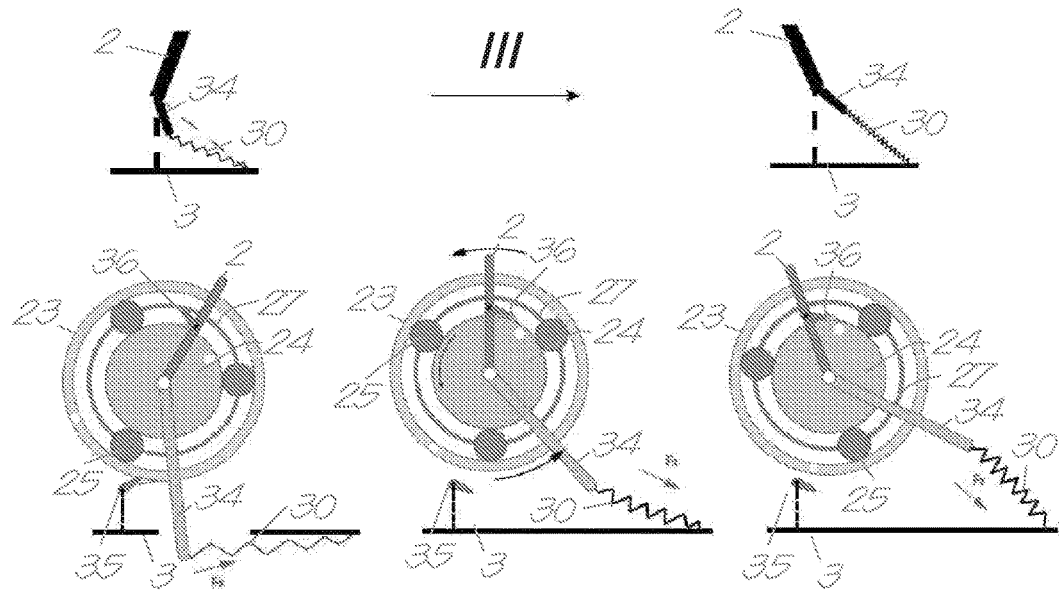

During the next phase III of plantar flexion, represented in FIGS. 14 to 16, the ratio adapting means are again arranged such that the first pawl 35 is in the unlocking position, whereas the second pawl 36 is in the locking position, resulting again in a conversion ratio 1.

As a consequence, the elastic behaviour of the prosthesis 1 according to the invention can be considered as being relatively flexible during this phase III.

So, the energy stored in the elastic element 30 during phase II by compressing it over a certain distance or angular range, is released during phase III by stretching the elastic element 30 again over the same distance or angular range.

However, during phase II the compression of spring 30 was obtained by only a relatively small angular change between the first body 2 and the second body 3 (±15°), due to the high conversion ratio applied, whereas said stored energy is released over a larger angular change between the first body 2 and second body 3 (±25°), due to the smaller conversion ratio applied during said phase III.

This is exactly what is required in order to better imitate the human body ankle joint.

Figures 17, 18, 19:
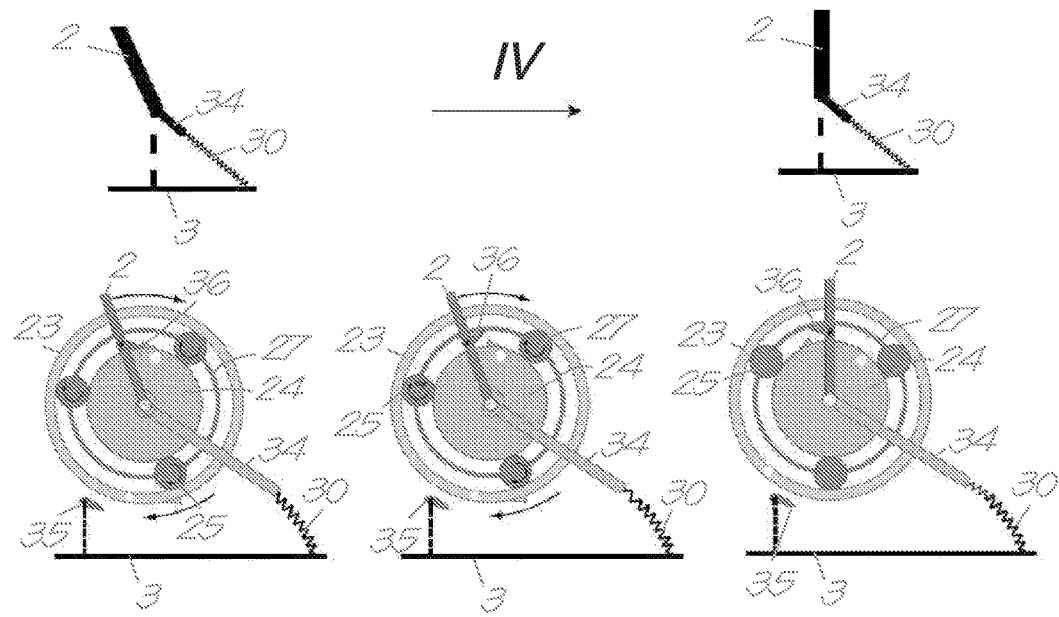

The last phase IV of the gait cycle is represented in FIGS. 17 to 19, during which phase IV almost no force is exerted.

The ratio adapting means are during this phase IV arranged in such a way that both pawls 35 and 36 are in the unlocking position.

Hereby, the sun wheel 24 is actually kept in an equilibrium position by the elastic element 30.

During rotation of the planet carrier 27 the planetary wheels 25 are turning around the sun wheel 24 driving the ring wheel 23 in the same sense as the planet carrier 27.

Since an angular change between the first body 2 and the second body 3 is not resulting in any angular change of the sun wheel 24 or lever arm 34, the conversion ratio applied by the converting mechanism is zero during this phase IV.

In order to have a small driving force for rotating the first body 2 with regard to the second body 3 during this phase IV, in practice a small additional spring element can be provided.

It is clear that a prosthesis 1 according to the invention is much more efficient than the existing ones, the behavior of the joint also being more close to the behavior of the human ankle joint.

In order to still improve the characteristics of the prosthesis, a prosthesis 1 according to the invention can additionally be provided with active pre-tension means arranged for changing the load on the elastic element 30 independently from the passive mechanical converting mechanism.

The reason for such an additional pre-tension means is that the curve 41 represented in FIG. 5 depends on the speed of walking.

So, said active pre-tension means could for example be controlled by control means 30B, which adapt the pre-tension on the elastic element 30 as a function of the walking mode.

In that way still an energy efficient prosthesis 1 or orthosis is obtained, since only a small amount of energy is to be added to the system for obtaining the required pre-tensioning, certainly when compared to the energy lost in the known prostheses of the active type.

The embodiment described here before just serves as an example and the invention is in no way restricted to said embodiment.

For example, in another embodiment other gears of the planetary system could be chosen for being the input or the output of the converting mechanism.

The converting mechanism could also be a completely different gear wheel system.

For example, the same result can be obtained by using any other kind of gear transmission box, wherein the conversion ratio can be changed during the gait cycle, for example as in a car gear box in which a choice can be made between a lot of pairs of transmitting gear wheels.

In still another embodiment the converting mechanism can for example comprise a differential gear system having a carrier in which two side gears are mounted opposite to one another in a rotatable manner, respectively on a first half shaft and a second half shaft, said first and second half shaft being aligned along the same axis, the side gears both intermeshing with two pinion gears which are mounted on pinion shafts in the carrier perpendicular to said axis, the pinion gears and side gears forming a cluster of four gears in a rectangle.

In another embodiment the converting mechanism can be provided with a pulley, a chain being provided over the pulley, one end of the chain being connected to a fixed point on one of the bodies, while the other end of the chain is connected to one of the ends of the spring.

Figure 20:
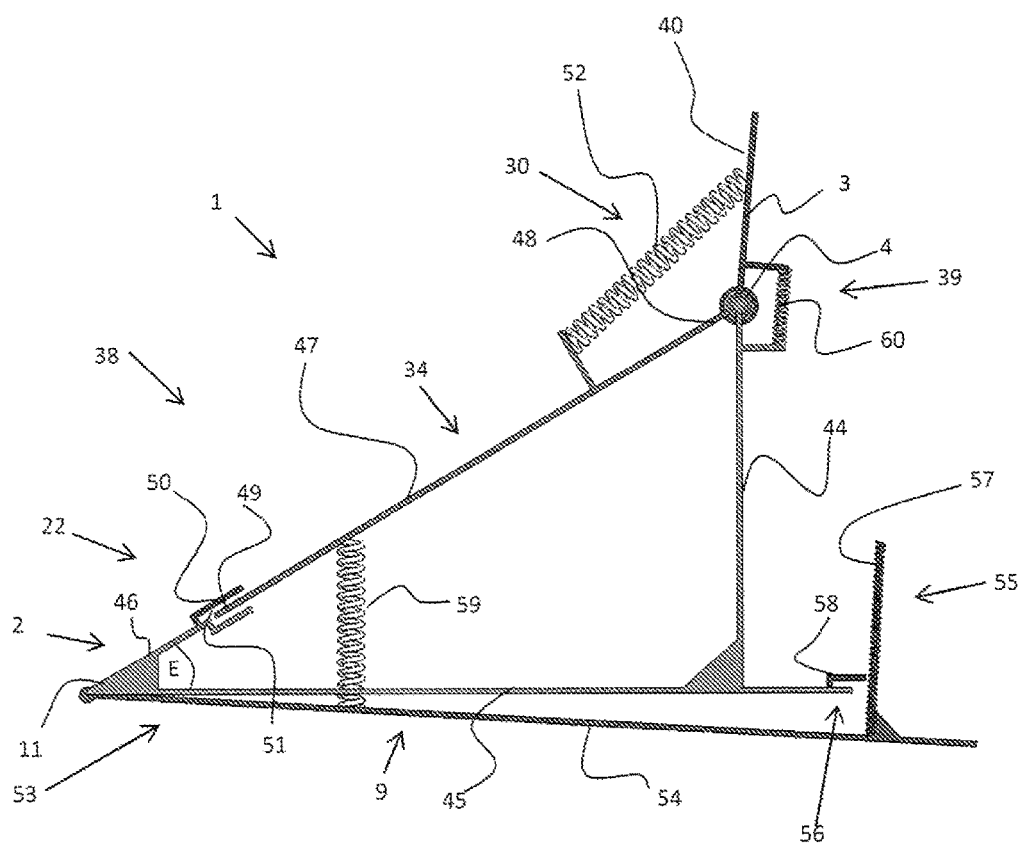
FIG. 20 represents in a schematic way another embodiment of a prosthesis in accordance with the invention.

In FIG. 20 another embodiment of a prosthesis 1 in accordance with the present invention is represented in a schematic way.

In this embodiment the prosthesis 1 is, as in the preceding example, provided with a first body 2, a second body 3 and an articulated joint 4 between said first body 2 and second body 3, the articulated joint 4 allowing a rotation of the first body 2 and the second body 3 with respect to one another.

In FIG. 20 the second body 3 is drawn as a line which schematically represents the lower leg 40 of a person.

The first body 2 is represented by lines 44 to 46 forming part of a rectangular triangle.

The lines 44 and 45 are perpendicular to one another and represent schematically a part of the heel and the sole 9 of a persons' foot 38 respectively.

The toe end 11 of line 45 is connected to line 46 forming an angle E of approximately 30° in order to represent in a schematic way the more or less triangular shape of a persons' foot 38.

The first body 2 and the second body 3 are connected to one another by means of the articulated joint 4 which is drawn as a hinge representing schematically an ankle joint 39.

As in the preceding embodiment, the prosthesis 1 of FIG. 20 comprises also a passive mechanical converting mechanism 22.

In this embodiment the passive mechanical converting mechanism 22 is however of a complete other nature, the passive mechanical converting mechanism 22 being not a planetary gear system.

In particular, the converting mechanism 22 comprises first of all a third body 34, drawn in FIG. 20 as a line 47 which is schematically representing the instep of a persons' foot 38.

This third body 34 is at a first end 48 hinge mounted in the articulated joint 4 which forms the ankle joint 39 and is therefore in principle arranged movably with respect to the first body 2 and to the second body 3 as in the above described embodiments of a prosthesis 1.

Nevertheless, the third body 34 is at its other end 49, which is directed towards the toe end 11 of the foot 38, provided with a first locking mechanism 50, by which a displacement or rotation of the third body 34 with respect to the first body 2 can be prevented.

In this case, the first locking mechanism 50 is realized by a groove 51, in which groove 51 the end 49 of the third body 34 can be introduced for being locked against a rotation or displacement with respect to the first body 2, or, in the opposite case, from which groove 51 the end 49 can be released again for allowing a rotation of the third body 34 with respect to the first body 2 around the ankle joint 39.

Furthermore, a first elastic element 30 is provided between the second body 3 and the third body 34, which is in this case represented schematically by a spring element 52 between the respective bodies 3 and 34.

However, the first elastic element 30 can be any other kind of an elastic element 30 which allows a rotation between the second body 3 and the third body 34 when torque is executed between the second body 3 and third body 34, the elastic element 30 being loaded or unloaded during such a rotation depending in case of storing or releasing mechanical energy.

The passive mechanical conversion mechanism 22 is furthermore provided with a fourth body 53 represented in FIG. 20 by lines 54 and 55 which are drawn perpendicular to one another.

The line 54 is again a schematic representation of a part of the sole 9 of the prosthesis 1, whereas the line 55 represents schematically a part 55 of a second locking mechanism 56 of the prosthesis 1.

The fourth body 53 is arranged movably with respect to the first body 2 by being hinge mounted at or near the toe end 11 of line 54, which represents part of the sole 9, to the first body 2.

Between the line 55 of the fourth body 53 and the first body 2 a second locking mechanism 56 is provided for keeping the fourth body 53 in a certain position with respect to the sole 45 of the first body 2.

This second locking mechanism 56 consists in the case represented in FIG. 20 of a kind of ratchet 57 in the form of a linear or curved rack with teeth, which is provided at the inside of the heel part 55.

The teeth on the rack 57 cooperate with a hook 58 provided on the sole 45 of the first body 2, as follows.

When the fourth body 53 is subjected to a force which tends to move the fourth body 53 away from the first body 2, i.e. a force which tends to move the fourth body 53 in a downward direction, such a movement is prevented by the teeth on the ratchet 57.

On the other hand, when the fourth body 53 is subjected to a force which tends to move the fourth body 53 towards the first body 2, i.e. a force which tends to move the fourth body 53 in an upward direction, such a movement is not prevented and the hook 58 is simply brought in a position between two teeth of the ratchet 7 nearer to the sole part 54 of the fourth body 53.

In a preferred embodiment of the prosthesis 1 represented in FIG. 20 one or more of the body parts, i.e. the first body 2, the second body 3, the third body 34 and/or the fourth body 53 are made of a more or less flexible material allowing considerable deformation during the gait cycle in order to realize in a smooth way the locking and unlocking of body parts with respect to one another by means of the first and/or second locking mechanisms 50 and 56, while storing or releasing mechanical energy by the elastic elements.

The third body 34 and the fourth body 53 of the passive mechanical conversion mechanism 22 are connected to one another by a second elastic element 59, which is in this case represented schematically by a spring element 59, but which can be according to the invention of any other suitable kind.

Finally, the prosthesis 1 of FIG. 20 is also provided with a small spring element 60 which connects the heel part 44 of the first body 2 to the second body 3.

As in the embodiment described before, the mechanical converting mechanism 22 of FIG. 20 is arranged for converting an angular change between the first body 2 and the second body 3 into a change of load on the elastic element 30.

Furthermore, the first locking mechanism 50 and the second locking mechanism 56 can be considered as being adapting means which interact with the mechanical converting mechanism 22 in such a way that the conversion ratio of the angular change during phase II, as represented in FIG. 4, is different from the angular change during phase III, during the gait cycle.

This embodiment of a prosthesis 1 according to the invention is particularly suitable for imitating the characteristics of a natural gait cycle.

Hereby, the curve 43 for this embodiment in which the moment force, exerted by the person walking or running with the prosthesis 1 is set against the angular change between the foot 38 of the prosthesis 1 and the lower leg 40 of the person, is closely resembling the curve 41 of the natural gait cycle, represented in FIG. 5.

The working principle of this embodiment of a prosthesis 1 in accordance with the invention is represented in FIGS. 21 to 25.

It is obvious that the FIGS. 20 to 25 are only schematic representations which are intended for simplifying the understanding of the working principles behind this embodiment of a prosthesis 1 in accordance with the invention and that these figures do not restrict the invention in any way whatsoever.

In FIGS. 21 to 25, it is illustrated how the different body parts are locked and unlocked by means of the first and second locking mechanisms 50 and 56 during the subsequent phases of the gait cycle I to IV in order to obtain the suitable conversion ratio by which the change of load on the elastic element 30 is performed.

Figure 21:
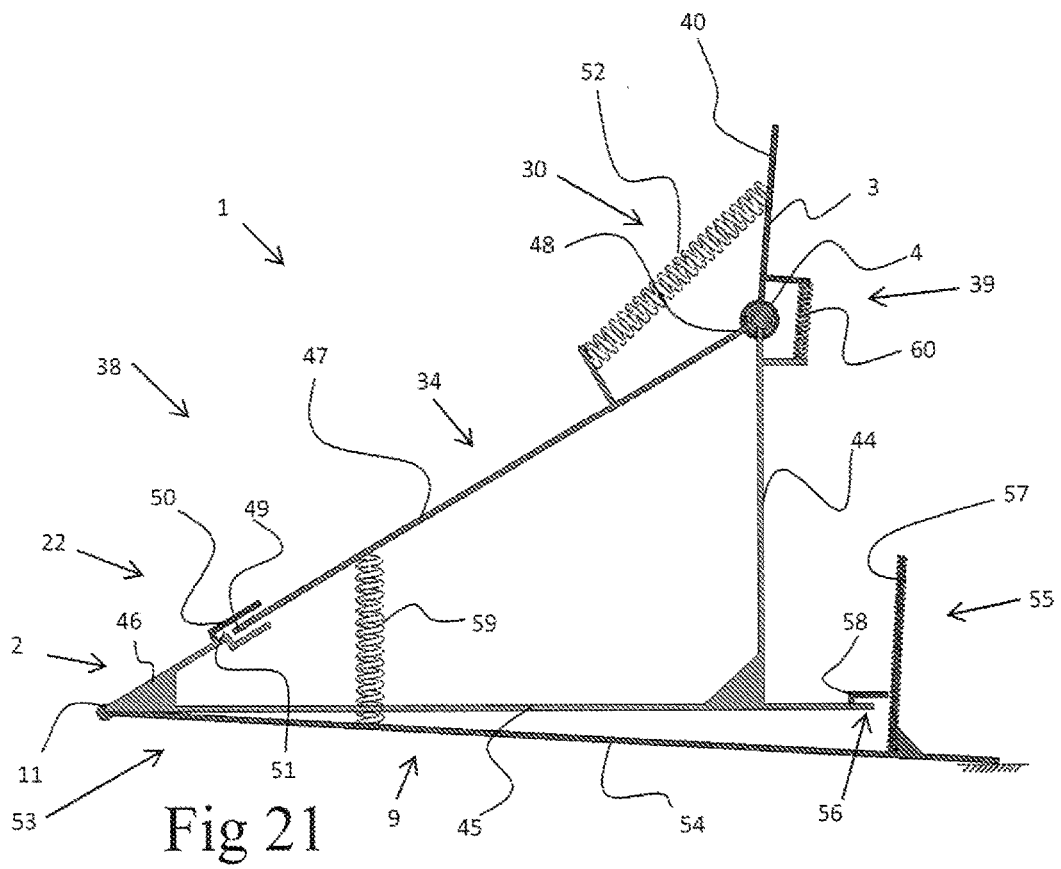
FIGS. 21 to 25 illustrate the prosthesis of FIG. 20 during successive stages in the gait cycle.
Figure 22:
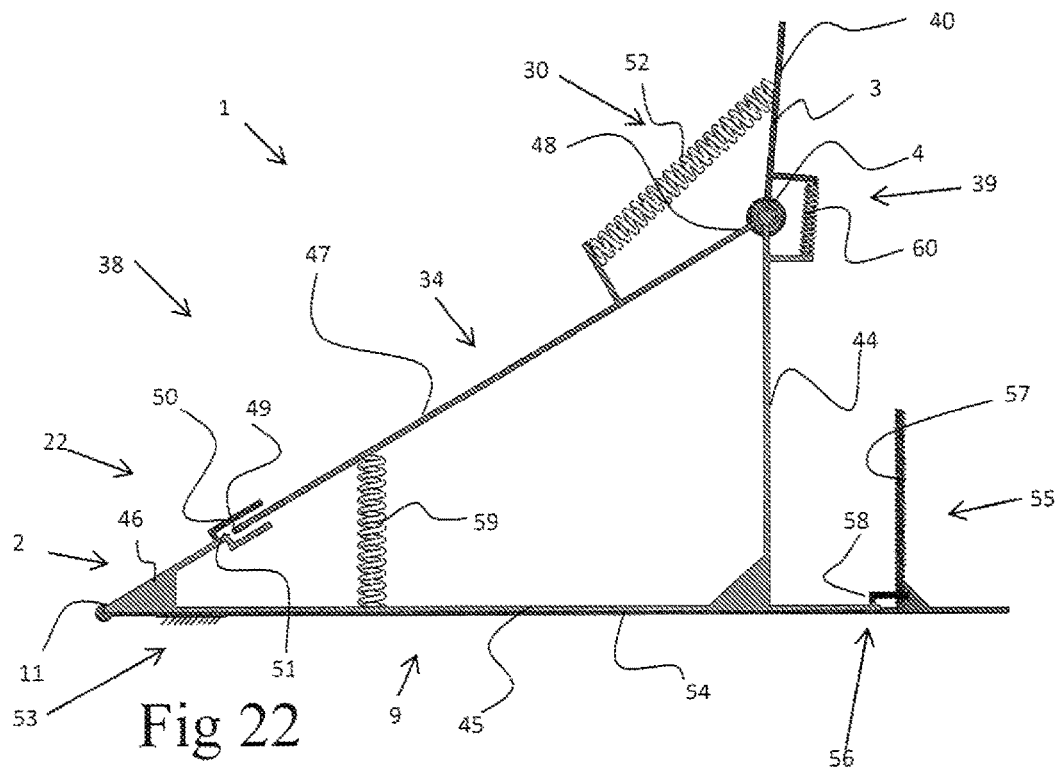

The situation in FIG. 21 corresponds with the start of the first phase I, as represented in FIG. 4, when the heel strikes the ground, whereas FIG. 22 corresponds with the end of phase I when the foot 38 is completely on the ground.

As can be derived from FIG. 21, at heel strike the third body 34 is locked in the first body 2 by means of the first locking mechanism 50.

On the other hand, at the start of phase I, the fourth body 53 is in the unlocked position, the hook 58 of the second locking mechanism 56 being disconnected from the teeth of the ratchet 57.

At that moment, the second elastic element 59 is used to set an initial angle between the first body 2 and the second body 3.

By contact of the heel on the ground the fourth body 53 is rotated around the hinge at the toe side 11 towards the sole part 45 of the first body 2.

During this rotation the hook 58 is systematically pushed over the teeth of the ratchet 57, so that the fourth body 53 is more and more locked in the ratchet 57 until the sole part 54 of the fourth body 53 is substantially coinciding with the sole part 45 of the first body 2.

This is the position illustrated in FIG. 22, the foot being flat on the ground and the second elastic element 59 being in the loaded, contracted condition by being compressed between the fourth body 53 and the third body 34.

Figure 23:
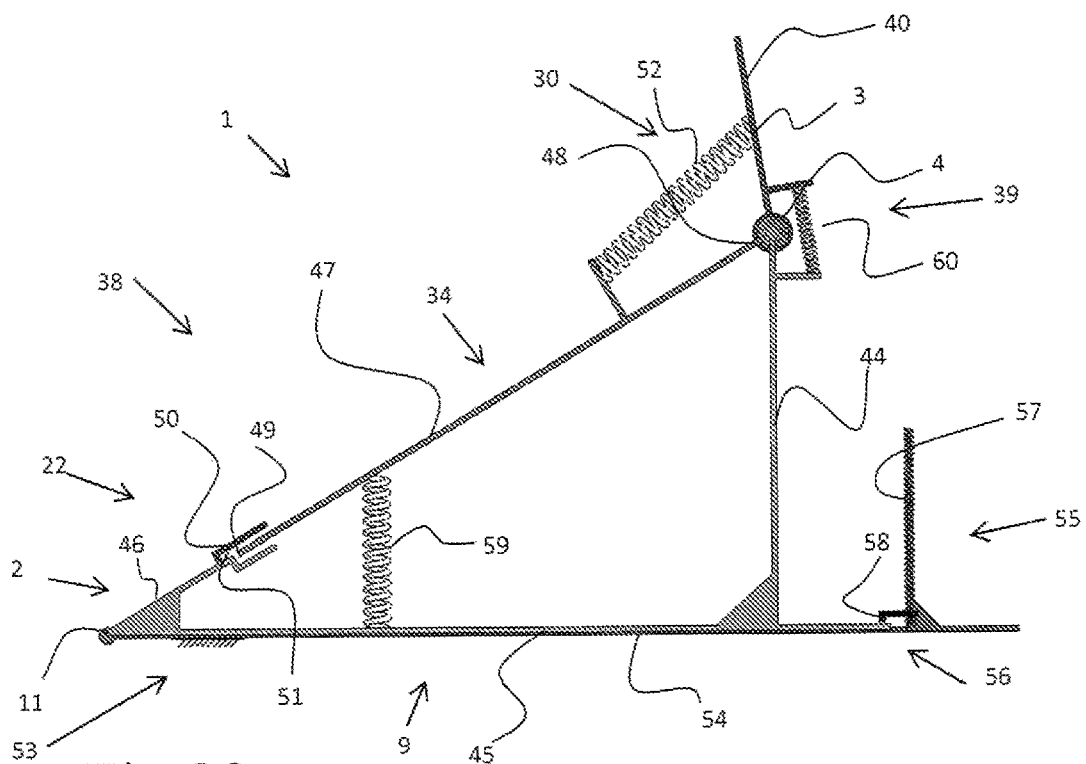

The next phase II or dorsal flexion phase II during which the lower leg 40 is brought forward while the foot 38 is kept on the ground, is illustrated in FIG. 23.

In this phase the third body 34 is still kept locked in the first body 2 by means of the first locking mechanism 50.

The first elastic element 30, represented in this case by spring element 52, is compressed during this phase II due to the rotation of the lower leg 40 towards the foot 38.

Hereby, energy is stored in the first elastic element 30, which corresponds to the situation in a natural gait cycle wherein energy is stored in the muscles during deceleration of the body.

In this situation the conversion ratio by which the passive mechanical conversion mechanism 22 is performing the angular change between the first body 2 and the second body 3 into a change of load on the elastic element 30 is only defined by the characteristics of the spring element 52 which represents the first elastic element 30, i.e. this first conversation ratio is defined by the stiffness of spring element 52.

Figure 24:
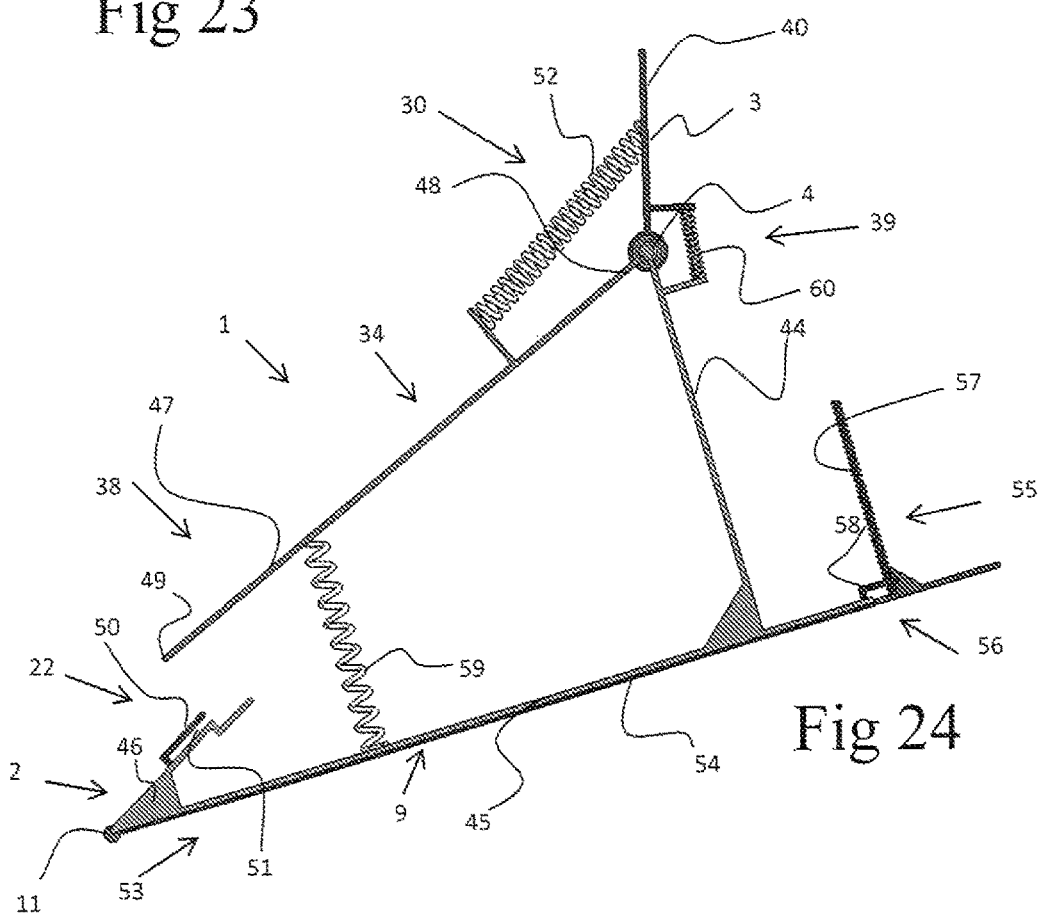

In FIG. 24 the next phase III, push-off or plantarflexion phase III is illustrated during which the foot 38 is pushed-off and is leaving the ground.

As can be seen in FIG. 24, in this phase III, the third body 34 is unlocked from the first body 2 by unlocking the first locking mechanism 50.

This unlocking is realized by releasing the end 49 of the third body 34 from the groove 51.

Of course it has to be understood that this unlocking action is preferably taking place in a natural way when a person walks with the prosthesis 1 in accordance with this embodiment, for example due to deformation or displacement of certain parts of the prosthesis 1 under the weight of the person.

The result of the unlocking of the third body 34 from the first body 2 is that the third body 34 is allowed to rotate around the ankle joint 39 and as a consequence that the second elastic element 59 is not any more stuck between a locked third body 34 and a locked fourth body 53.

This means that actually the first body 2 and the second body 3, which correspond respectively to the foot 38 and the lower leg 40, are in connection to one another by an elastic system formed by the first elastic element 30 and the second elastic element 59 being positioned in series to one another.

As a consequence, in this phase III, the conversion ratio by which the passive mechanical conversion mechanism 22 is performing the angular change between the first body 2 and the second body 3 on the elastic element 30 is now defined by the combination of the characteristics of the spring element 52, which represents the first elastic element 30, with the spring characteristics of the second elastic element 59.

So, the passive mechanical conversion mechanism 22 performs an adapted second conversion ratio during this phase III which is defined by the allover stiffness of the elastic system formed by the spring element 52 and the second elastic element 59 put in series.

It is also easily understood that the behavior during phase II is a more stiff behavior than during phase III, which means that a certain amount of energy is stored during phase II due to an angular change between the foot and the leg which requires however a relatively high torque, whereas the energy stored in phase I and II is released during phase III whereby an even higher torqueis delivered to the foot and the leg, while at the same time a relatively bigger angular change between the foot and lower leg is nevertheless obtained.

This corresponds to the requirements of a curve 41 of the human ankle joint.

It is therefore clear that by choosing a suitable stiffness for both said elastic elements 52 and 59 the characteristics of the curve 43 can be adapted and brought in conformity or at least approximately in conformity with the curve 41 of a natural gait cycle.

At the end of phase III the elastic elements 52 and 59 have released all their energy for accelerating the walking person, so that the elastic elements 52 and 59 are in their unloaded condition.

Figure 25:
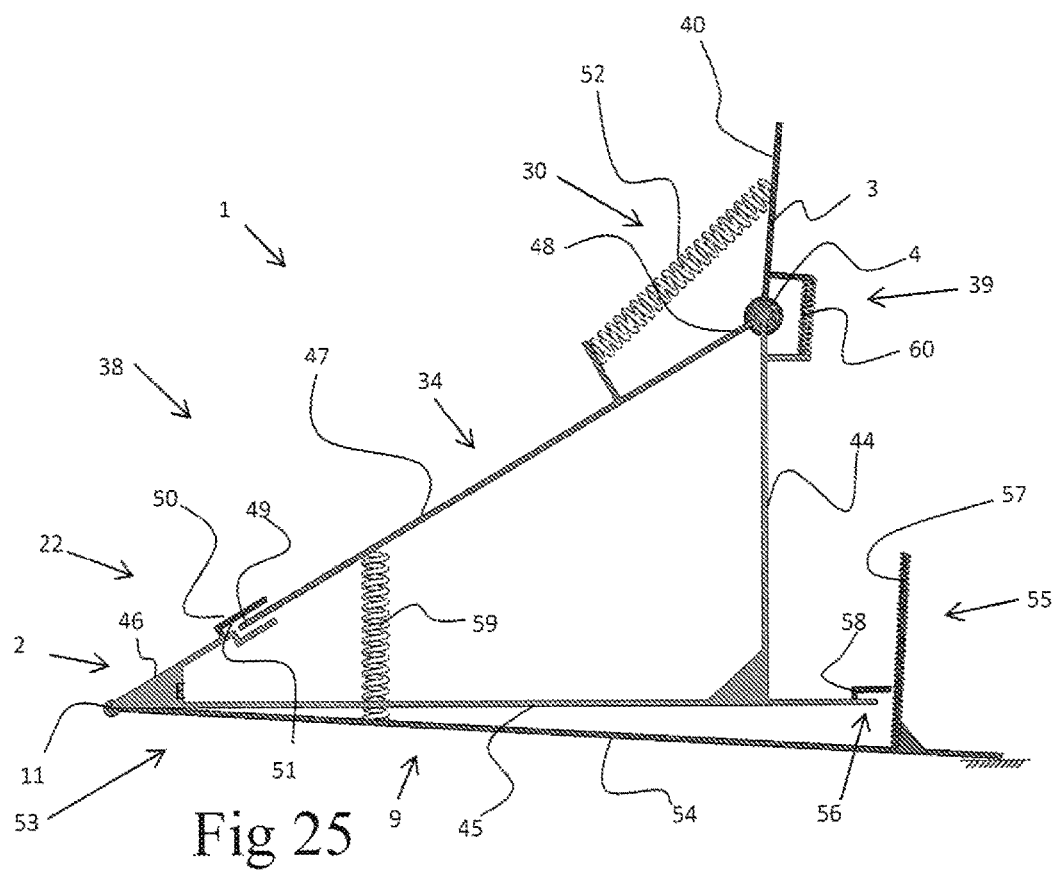

The final so-called swing phase IV of the leg 40, during which the foot 38 is rotated around the ankle 39 in order to bring the foot 38 back in its original position at heel strike, is illustrated in FIG. 25.

In this phase IV the foot 38 and lower leg 40 undergo a rotation which requires only a small torque due to the fact that the foot 38 is not touching the ground.

This rotation is performed by the small spring element 60 between the first body 2 and the second body 3.

At the same time, the fourth body 53 is again unlocked from the first body 1 by unhooking the hook 58 from the ratchet 57, while the third body 34 is again brought in the locked position with respect to the first body 2, the end 49 of the third body 34 being introduced again in the groove 51 of the first locking mechanism 50.

During this movement the first and second elastic element 52 and 59 are kept of course unloaded.

In this manner the cycle is closed.

Figure 26:
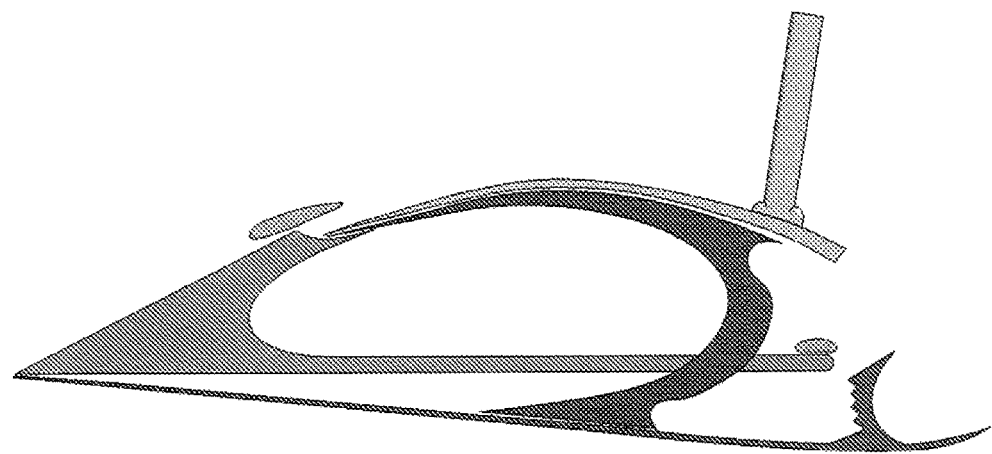
FIG. 26 represents a possible more realistic version of the embodiment illustrated schematically in FIG. 20.

In FIG. 26 a possible more realistic version of the embodiment of the prosthesis 1 of FIG. 20 is illustrated.

From this illustration it is clear that the elastic elements used for realizing the passive mechanical conversion mechanism are not necessarily spring elements, but can be formed by material parts of the prosthesis 1 itself which are made of more or less flexible materials.

Also the ankle joint 39 or articulated joint 4 is realized in this more practical version by a fixed connection between the third body 34 and the second body 3.

The third body 34 is however made of a rather flexible material, so that an angular change between this third body 34 and the lower leg 40 represented by the second body 3 is easily realized by deformation.

It is also obvious that other embodiments of the described prosthesis 1, having for example other kinds of joints, locking mechanisms, elastic elements or body parts, are not excluded from the invention.

Figure 27:
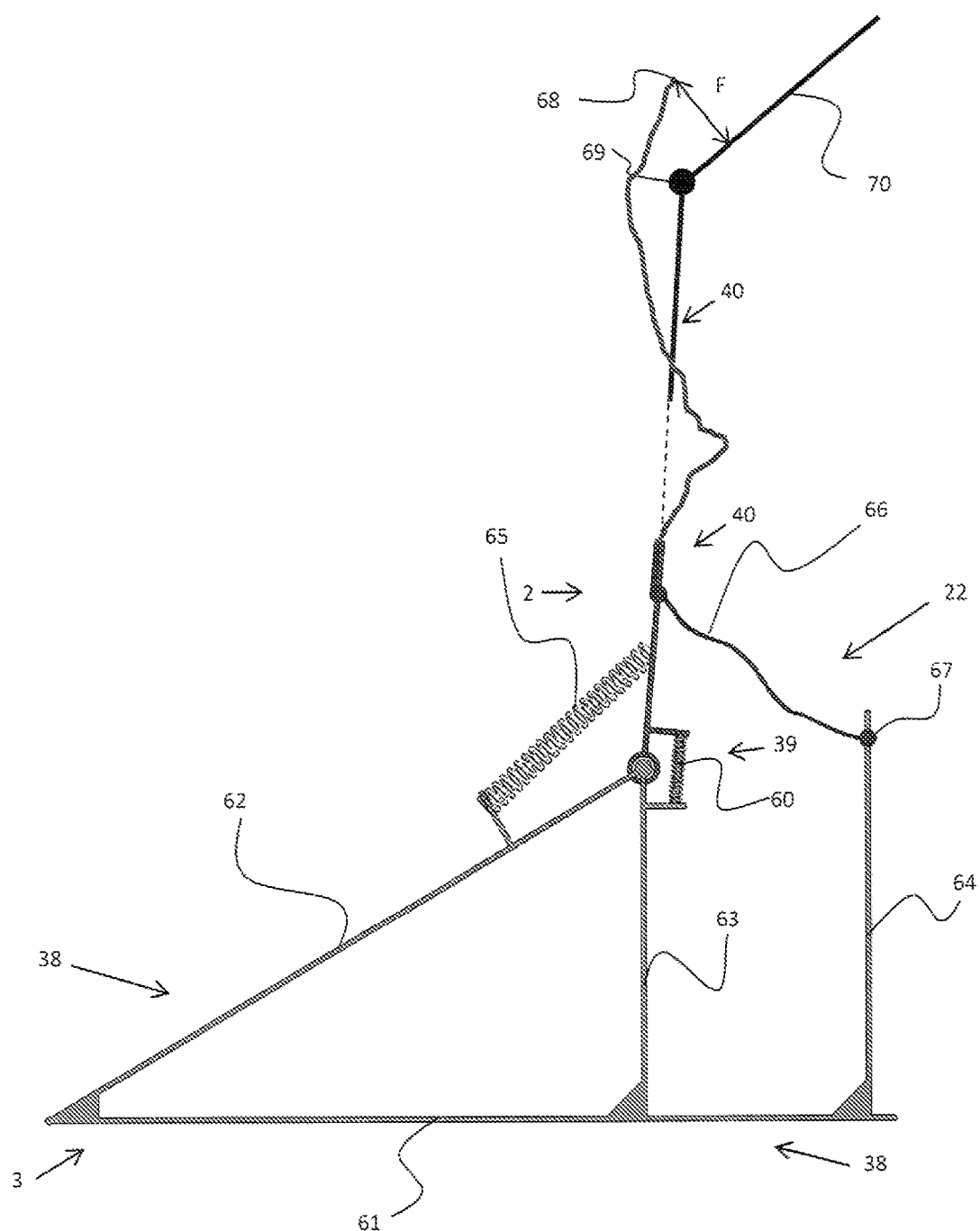
FIG. 27 represents in a schematic way still another embodiment of a prosthesis in accordance with the invention.

FIG. 27 represents still another embodiment of a prosthesis 1 in accordance with the present invention.

This embodiment of a prosthesis 1 according to the invention is especially interesting for persons which still dispose of certain tendons in their knee, which can additionally be used for manipulating the movement of the prosthesis 1 as well.

The general structure of the prosthesis 1 itself is somewhat more simple than in the preceding case.

As before, the prosthesis 1 comprises a first body 2 and a second body 3 connected to one another by an articulated joint 4 for rotational movement of the first body 2 and second body 3 with respect to one another.

The first body 2 is in this embodiment represented by the lower leg 40, drawn in the figures as a line 40.

On the other hand, the second body 3 is in this case a body 3 representing a foot 38, which is drawn in FIG. 27 in a schematic way by lines 61 to 64.

Line 61 is hereby representing the sole 9 of the foot 38, line 62 the instep of the foot 38 and line 64 the heel of the foot 38.

Line 63 is drawn perpendicular from the sole line 61 up to the articulated joint 4, so that lines 61, 62 and 63 are forming a rectangular triangle, which represents more or less the part of the foot 38 from the toe end 11 to the ankle joint 39.

The heel line 64 is drawn perpendicular to the sole line 61 and is again a schematic representation of a real body.

The prosthesis 1 according to the embodiment represented in FIG. 27 is also provided with a passive mechanical converting mechanism 22.

Nevertheless, this passive mechanical converting mechanism 22 is somewhat different from the passive mechanical converting mechanisms 22 described before and it can even be considered as being a simplified form or an example of a more generally described form of such passive mechanical converting mechanisms 22.

Hereby, the passive mechanical converting mechanism 22 represented in FIG. 27, comprises, as in preceding examples, an elastic element 65, which is mounted between the first body 2 and the second body 3 for absorbing and releasing energy during the gait cycle, and which is represented in FIG. 27 by a spring element 65.

The passive mechanical converting mechanism 22 comprises also a small spring element 60, as in the preceding case, which is only intended for returning the foot part of the prosthesis 1 during phase IV of the gait cycle to its original position relative to the lower leg part 40, the foot being in the air and the elastic element 65 being essentially unloaded at that time.

The passive mechanical converting mechanism 22 comprises also a cable 66 which is connected at one side 67 to the heel part 64 of the first body 2.

At its other side 68, this cable 66 is also connected to the knee joint 69 of the person.

In particular, the connection of the cable 66 is preferably connected at a certain offset distance F from the knee joint 69 and is guided through different parts of the lower leg 40, so that a rotation of the upper leg 70 with respect to the lower leg 40 results in a shorter or longer distance between the first end 67 of the cable 66 and the second end 68 of the cable 66.

As a consequence, a movement in the knee joint 69, which corresponds to a relative rotation of upper leg 70 and lower leg 40, can be related to an action on the foot 38, which is formed by a prosthesis 1, by tensioning or releasing the cable 66.

In another embodiment, cable 66 could be connected to a compressive (elastic) part of the lower leg 40, so that a shorter or longer distance between the first end 67 of the cable 67 and the second end 68, connected to the compressive part, of the cable 66 is related to the amount of compression.

As a consequence the motion of the compressive part is related to the tensioning and releasing of cable 66.

As will be explained hereafter, the behavior of a prosthesis 1 according to this embodiment of the present invention is quite similar.

According to the invention the triangular shape formed by the lines 61 to 63 can be considered as being the cross section of a solid material body having a more or less pyramid shape.

On the other hand it is not excluded from the invention to realize a prosthesis 1 which is substantially hollow for accommodating the parts of the passive mechanical converting mechanism 22.

Furthermore, in the representation of FIG. 27 the heel part 64 to which the cable 66 is connected is just a line 64, but of course this is just a schematic representation in order to define a part on the foot 38 to which the cable 66 is connected.

By means of FIGS. 28 to 32, the working principle behind the embodiment of a prosthesis 1 according to the invention, as represented in FIG. 27, will now be described.

Figure 28:
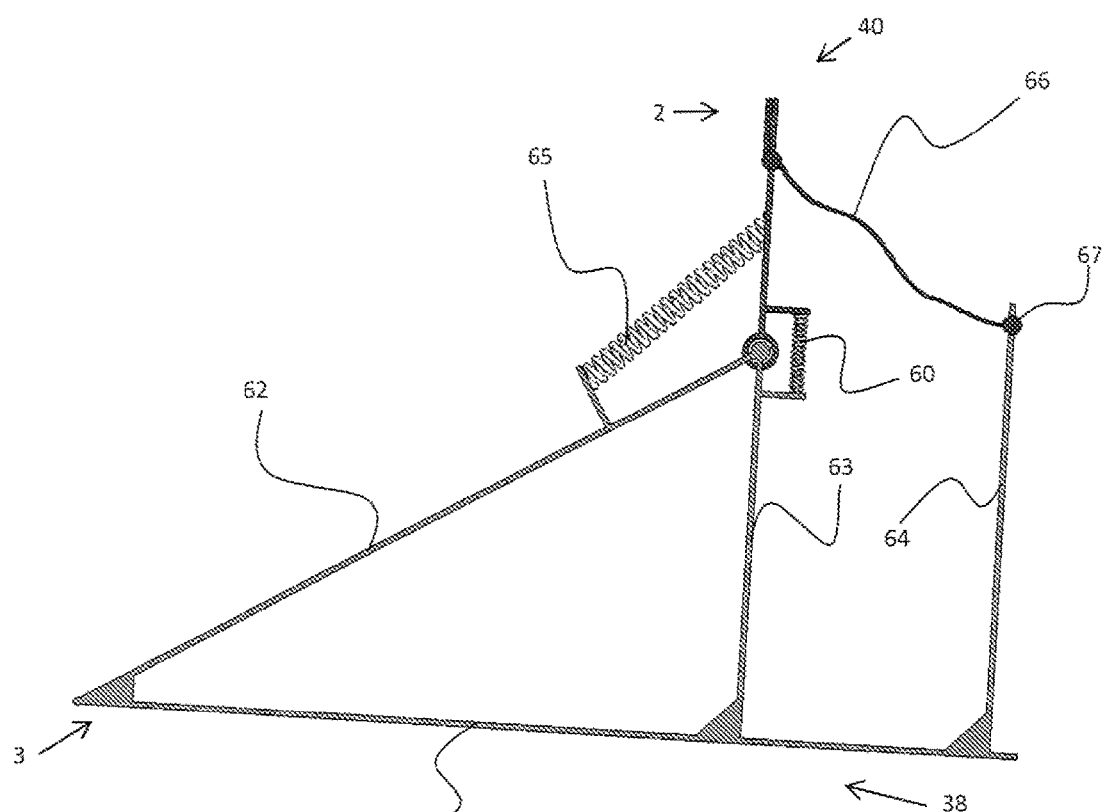
FIGS. 28 to 32 illustrate the prosthesis of FIG. 27 during successive stages in the gait cycle; and, FIGS. 33 and 34 represent schematically still other embodiments of a prosthesis in accordance with the invention.
Figure 29:
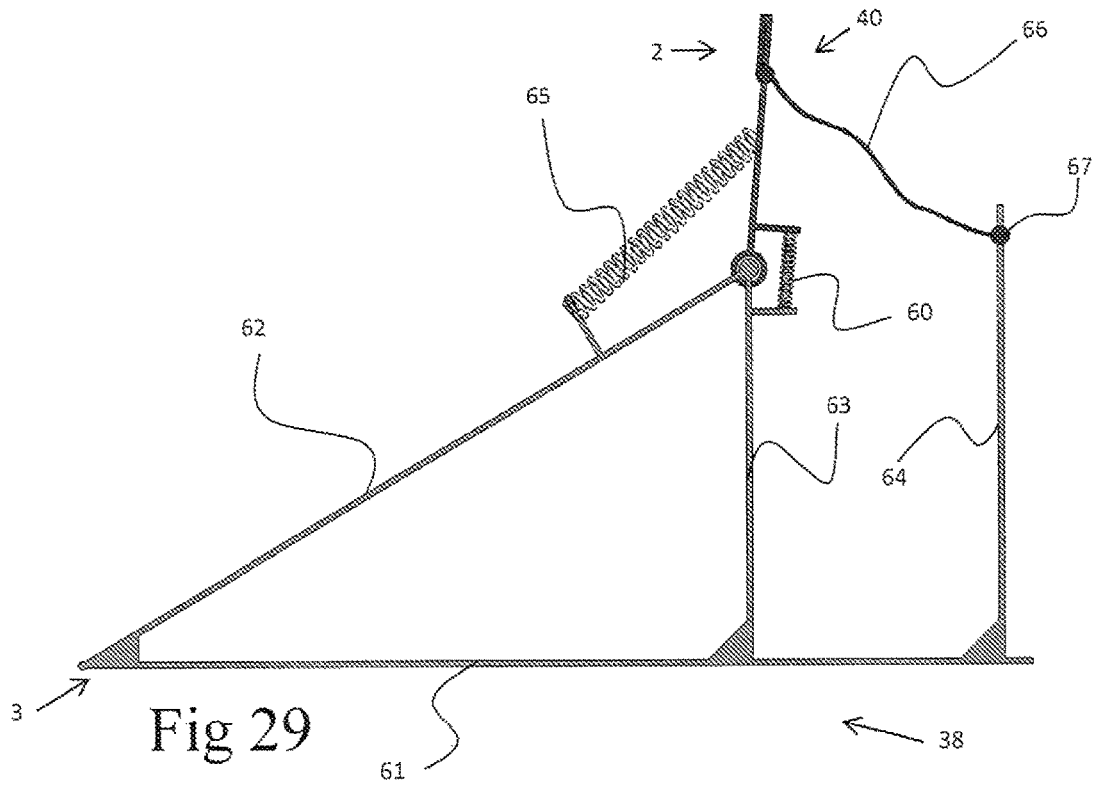

Phase I of the gait cycle is demonstrated in FIGS. 28 and 29, respectively in the starting position of phase I of the gait cycle, wherein the heel 64 is touching the ground, and in the end position of phase I of the gait cycle wherein the foot 38 is placed entirely on the ground with its' sole 61.

In FIG. 28, the foot 38 is just touching the ground and the spring element 65 is not loaded at that moment.

Also the cable 66 is, in this starting situation of phase I, not loaded at all, but rather not tensioned.

In the situation of FIG. 29, wherein the sole 9 of the prosthesis 1 is turned and is flat on the ground, the cable 66 is still not stretched, while the spring element 65 is slightly loaded.

Figure 30:
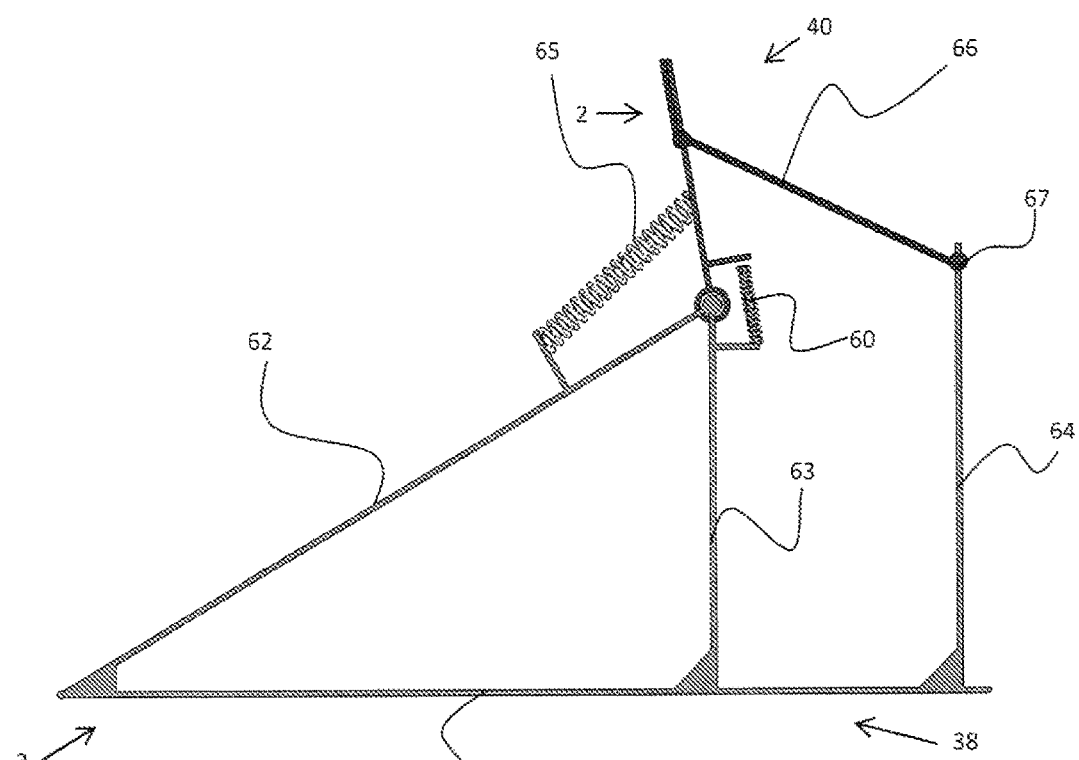

FIG. 30 represents the situation at the end of phase II of the gait cycle.

In this situation the spring element 65 is loaded in compression corresponding to a minimal relative angle between the first body 2 and the second body 3.

At the same time the cable 66 is just stretched due to a relative rotation of the upper leg 70 with respect to the lower leg 40.

Figure 31:
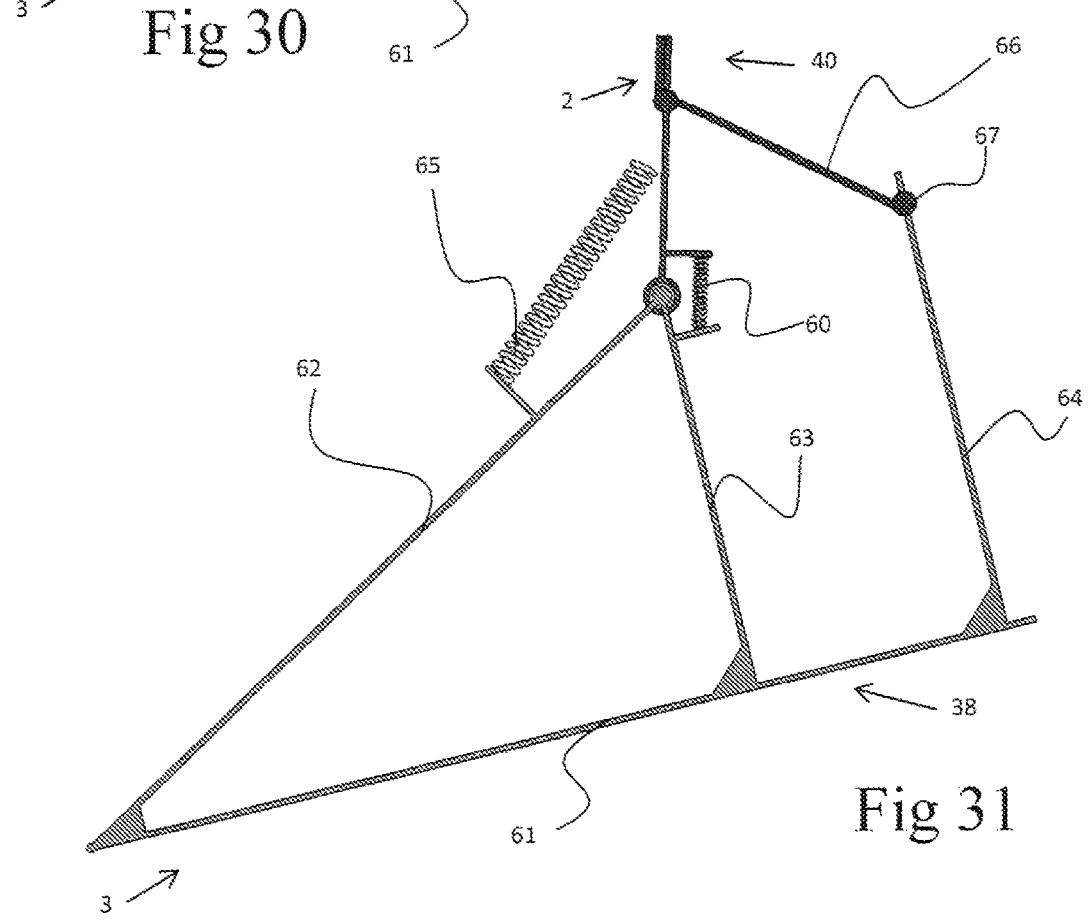

In FIG. 31 the situation is represented of phase III of the gait cycle.

At the end of phase III, the spring element 65 is unloaded, indicated in FIG. 31 by the fact that the spring element 65 is not touching any more the lower leg 40.

During the same phase III, the cable 66 is pulled further due to the rotation of the upper leg 70 with respect to the lower leg 40, so that the tension in cable 66 contributes to a further rotation of the lower leg 40 relatively to the foot 38.

The cable 66 is giving during this phase III of the gait cycle an additional torque to the ankle joint 39, which means that the passive mechanical converting mechanism 22 is actually arranged as in the preceding embodiments in such a way that the stiffness of the ankle joint 4 is higher during phase II than during phase III of the gait cycle, so that again the characteristic curve 43 for the prosthesis resembles the curve 41 of the human ankle joint 4.

Figure 32:
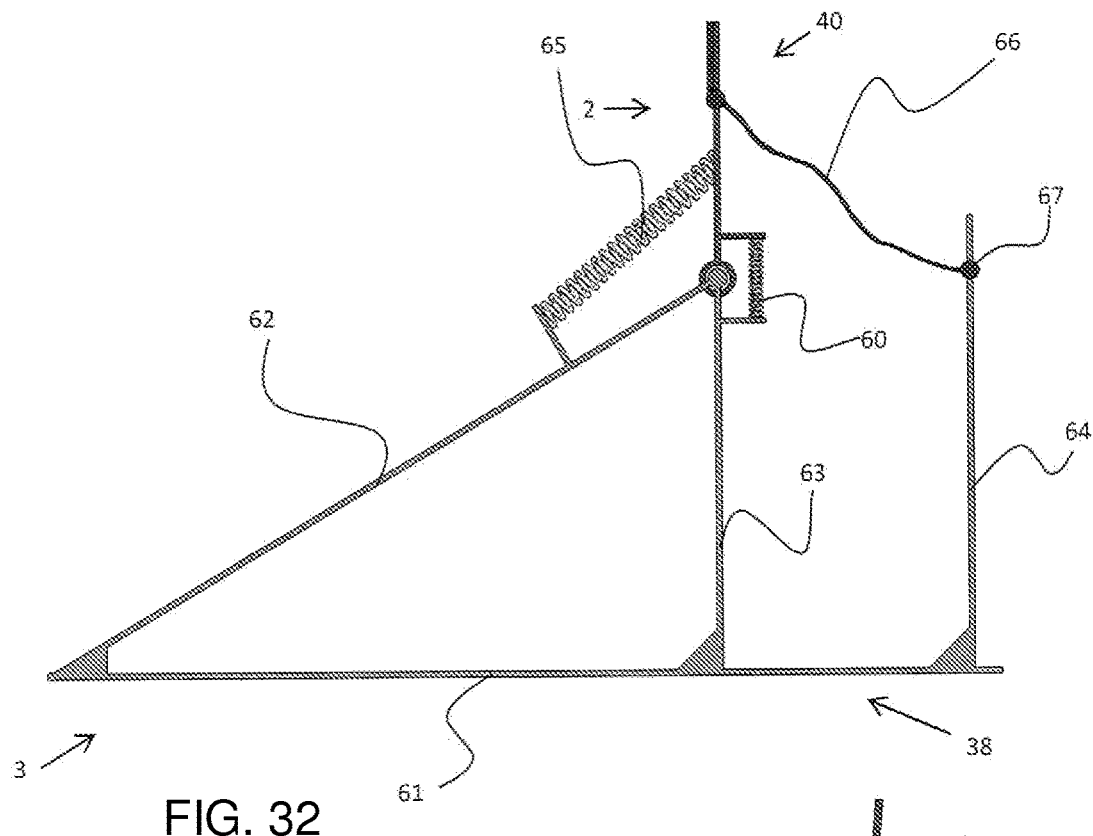

Finally, in FIG. 32 the end of phase IV is represented.

In this situation the upper leg 70 has been rotated back in respect of the lower leg 40, which results in the cable 66 being slack again.

The prosthesis 1 according to the embodiment described in FIG. 27 is different from the preceding cases in that said prosthesis 1 provides a mechanism not needing a third body as described before, at least not a third body which is integrated in the prosthesis 1 itself.

On the other hand, in this embodiment the upper leg 70 could be considered as being a third body, whereby the ratio adapting means are formed by the combination of the ankle joint 4 and the knee joint 69 and dependent on the relative rotational position of the lower leg 40 and upper leg 70 around the knee joint 69 as well as the relative rotational position between the foot 38 and the lower leg 40 a conversion ratio of the passive mechanical converting mechanism 22 is set.

Hereby, the elastic element is represented by the cable 66 between the heel 64 of the second body 3 (representing the foot 38) and the upper leg 70 (representing the third body).

The load on this cable 66, in particular whether the cable is in tension or is slack, is hereby clearly set by the ratio adapting means, i.e. by said relative position of foot 38, lower leg 40 and upper leg 70.

A possible more general way of describing the invention, i.e. an alternative formulation for claim 1, could therefore be as follows:

A prosthesis or orthosis for an ankle or any other joint comprising a first body, a second body and an articulated joint between said bodies, the articulated joint allowing the rotation of said bodies with respect to one another, a passive elastic mechanism in which energy is stored or from which energy is released in function of the relative position between the bodies, the passive elastic mechanism providing a stiffness to the articulated joint and wherein passive mechanical means are provided for modifying the elasticity of the passive elastic mechanism in order to set the stiffness of the articulated joint.

Figure 33:
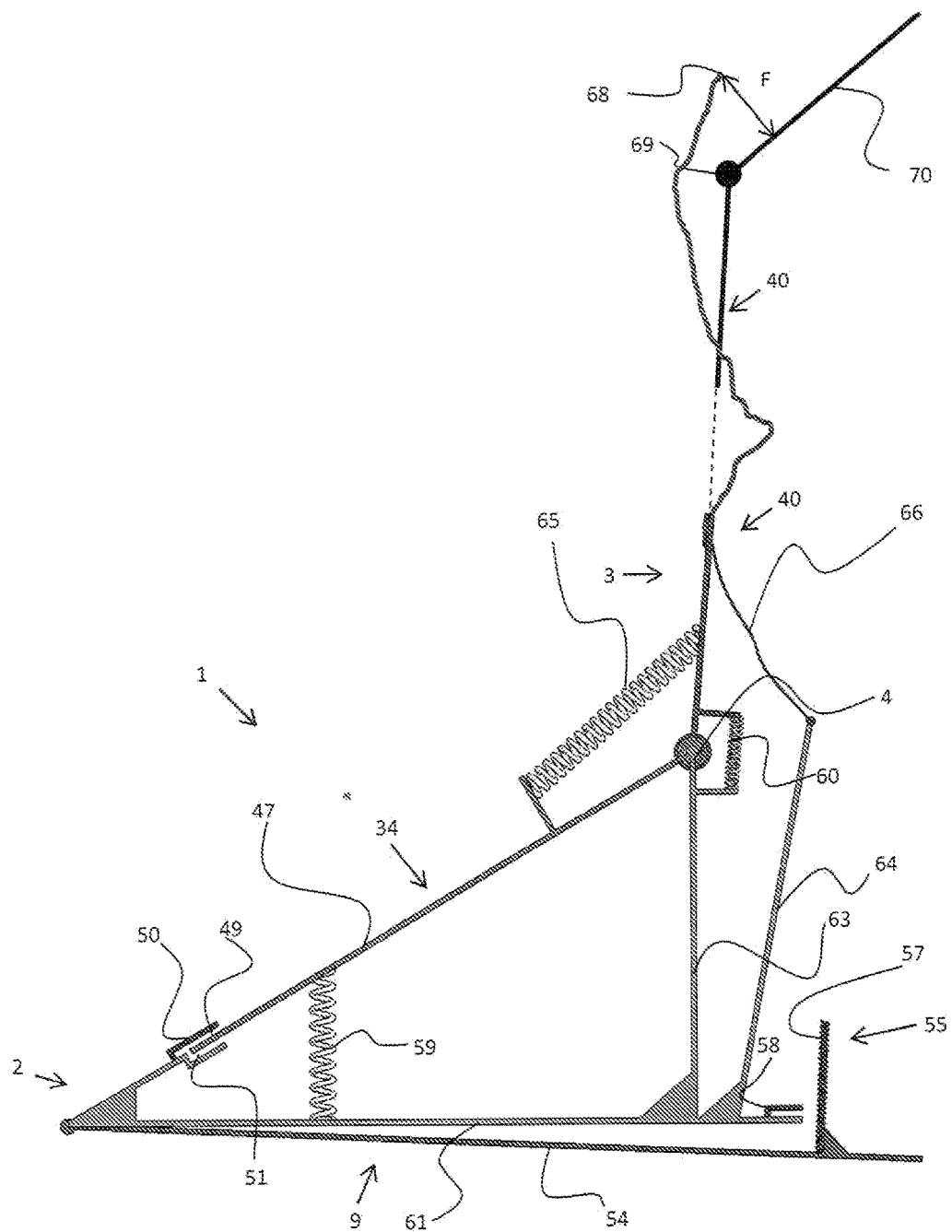

FIG. 33 represents still another embodiment of a prosthesis 1 in accordance with present invention, which is actually a combination of the embodiments represented in FIG. 20 and in FIG. 27.

As in the embodiment of FIG. 20, the prosthesis 1 comprises again a first body 2 representing a part of a foot 38, a second body 3, representing a lower leg 40, an ankle joint 4 between said first body 2 and second body 3 provided with elastic elements 65 and 60, a third body 34 and a fourth body 53 which are completely similar to the third body 34 and fourth body 53 of FIG. 20 and which are lockable by means of first and second locking mechanisms 50 and 56 and wherein a second elastic element 59 is provided.

The only difference with the situation of FIG. 20 is that the first body 2 is realized as the foot 38 represented in FIG. 27, wherein additionally a heel part 64 is provided which extends perpendicular on the sole 61 of the foot 38.

Hereby, as in the embodiment of FIG. 27, a cable 66 is connected between said heel part 64 and a tendon 68 on the upper leg 70.

The working principle of this embodiment of a prosthesis 1 according to the invention is similar to what has been described before and needs no further comment.

The biggest advantage of this embodiment is that the forces on the elastic elements 59, 65 as well as in the cable 66 can be kept smaller than in the preceding embodiments.

Figure 34:
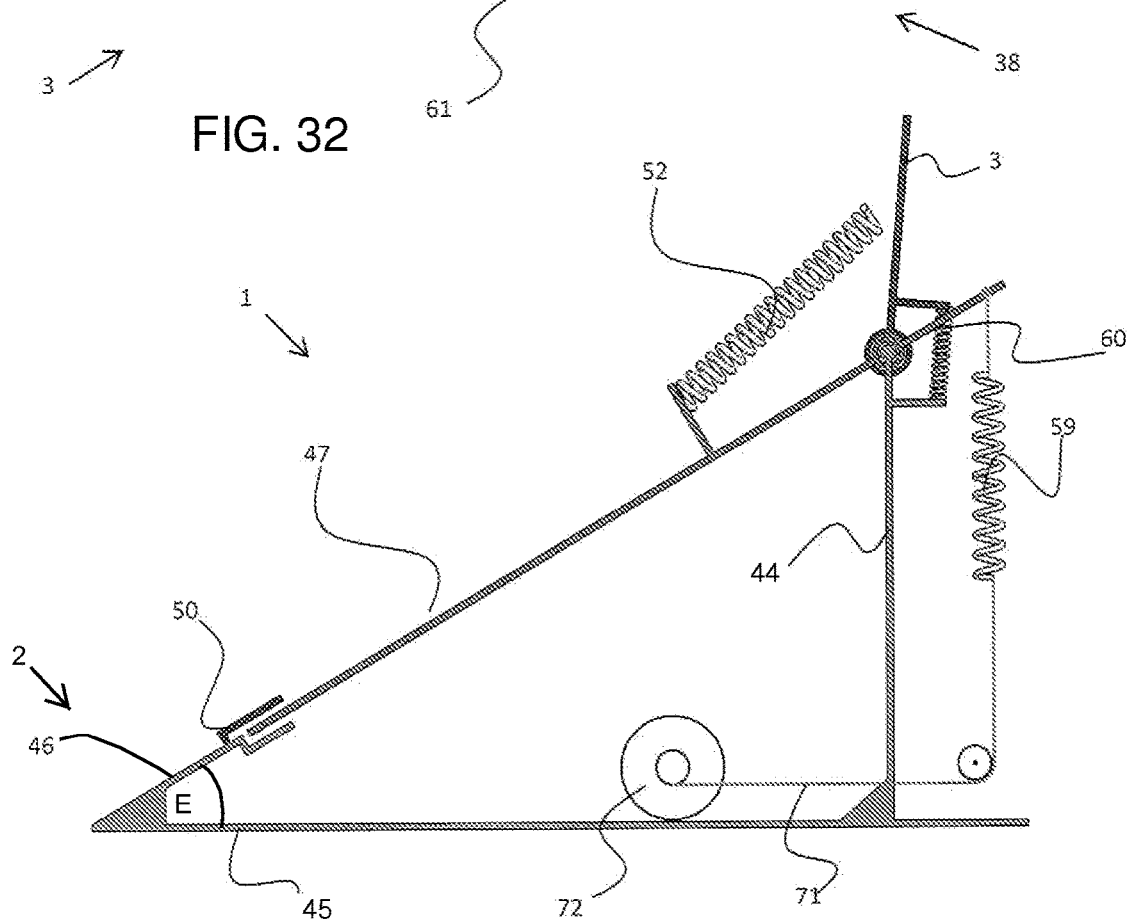

In FIG. 34 another embodiment of a prosthesis 1 is illustrated, which is a version that differs slightly from the embodiment described with respect to FIG. 20.

In this embodiment the fourth body 53 has been omitted.

The reason is that in the embodiment of FIG. 20, the elastic element 59 is compressed due to the weight acceptance of the walking person in phase I of the gait cycle.

Hereby, the foot plate formed by the fourth body 53 is rotated towards the first body 2.

The compression of elastic element 59 could possibly be felt by the walking person and could be unpleasant.

Therefore it is proposed in this embodiment to provide active means in the form of an electric motor for compressing the elastic element 59.

The case represented in FIG. 34 is still somewhat different in that the elastic element 59 is arranged between the third body 34 and the first body 2 at the right hand side of the articulated joint and as a consequence said elastic element 59 needs to be tensioned instead of being compressed in order to obtain the same functioning of the prosthesis 1.

Hereby, the elastic element 59 is at one end provided with a cable 71 which can be wind or unwind on a spool by means of an electric motor 72, so that the tensioning of the elastic element 59 is realized by active means.

The tensioning can be realized in the whole period during which the third body 34 is locked in the first body 2, which is during about 80% of a stride.

On the other hand, the electric motor 72 will unwind the cable 71 to its original position in the remaining 20% of a stride, no load being applied on the elastic element 59 during that period.

As a consequence, the electric motor 72 can work with considerable less power.

Although in this embodiment of a prosthesis 1 in accordance with the present invention, the mechanical converting mechanism 22 is not completely passive anymore, it is still advantageous over the known prostheses with active means due to the reduced power needed.

Of course, it is not excluded from the invention to combine features of the different embodiments described.

A prosthesis or orthosis in accordance with the invention can, apart from its application as an ankle, also be used for other parts in the human body as for example a knee or an elbow or the like.

It is even possible to use such a prosthesis or orthosis in accordance with the invention in a complete other domain of application, as for example in the domain of robotics, for instance for connecting two parts of a robot in a rotatable manner by means of an articulated joint and elastic element as described, in order to ameliorate the movements in such a robot or to increase its efficiency.

The present invention is in no way limited to the embodiments described above and represented in the drawings, but such a prosthesis or orthosis may be realised in different shapes and dimensions, using a method according to the invention which is different from the above-described, without departure from the scope of the invention.

The invention claimed is:

1. A prosthesis or orthosis for an ankle or any other joint comprising:
    a first body, a second body and an articulated joint between said bodies, the articulated joint allowing the rotation of said bodies with respect to one another;
    a mechanical converting mechanism including a third body, said mechanical converting mechanism being a passive mechanical converting mechanism, said third body arranged movably with respect to said first body and said second body;
    an elastic element affixed on said third body and/or said second body in a configuration that stores energy in the elastic element during a dorsal flexion phase of a gait cycle;
    said mechanical converting mechanism being disposed for converting an angular change between said first body and said second body, indicated as an input angular change, into a change of load on said elastic element, the converting resulting in a change at an output of said mechanical converting mechanism for stretching or compressing the elastic element; and
    ratio adapting means interacting with said mechanical converting mechanism arranged for modifying a conversion ratio by which the change of load on the elastic element is performed, said ratio adapting means setting the conversion ratio, the conversion ratio being defined as an amplitude of change at said output of said mechanical converting mechanism divided by the input angular change.

2. The prosthesis or orthosis according to claim 1, wherein the converting of the mechanical converting mechanism results in a change at the output of the mechanical converting mechanism, which is an output angular change applied between said second body and said third body.

3. The prosthesis or orthosis according to claim 1, wherein a combination of said elastic element with said mechanical converting mechanism forms an elastic system mounted between said first body and said second body, which elastic system has a stiffness that is set independently from a stiffness of said elastic element thereof by setting the conversion ratio for the converting mechanism thereof with the ratio adapting means.

4. The prosthesis or orthosis according to claim 1, wherein:
    said elastic element is part of a passive elastic mechanism in which energy is stored or from which energy is released as a function of the relative position between the bodies, the passive elastic mechanism providing a stiffness to the articulated joint; and
    the ratio adapting means is provided for modifying the elasticity of the passive elastic mechanism in order to set the stiffness of the articulated joint.

5. The prosthesis or orthosis according to claim 1, wherein due to a change of angular position between said first body and said second body out of an equilibrium position, energy is stored in said elastic element.

6. The prosthesis or orthosis according to claim 1, wherein said elastic element allows a rotation between said second body and said third body when torque is executed between said second body and said third body, said elastic element being loaded or unloaded during such a rotation depending on whether the elastic element is storing or releasing mechanical energy.

7. The prosthesis or orthosis according to claim 1, wherein energy is stored in said elastic element due to a rotation of said first body towards said second body.

8. The prosthesis or orthosis according to claim 1, wherein said ratio adapting means is formed by a locking mechanism.

9. The prosthesis or orthosis according to claim 1, wherein the articulated joint includes a shaft mounted rotatably on said second body, said shaft additionally being mounted fixedly with respect to said first body.

10. The prosthesis or orthosis according to claim 1, wherein said first body and said second body are coupled at one end to each other by the articulated joint, said first body and said second body extending from said articulated joint and defining extending body parts.

11. The prosthesis or orthosis according to claim 1, wherein said ratio adapting means are such that during a relative rotation of said first body and said second body in a first sense, the conversion ratio is different from the ratio performed during a relative rotation of said first body and said second body in the opposite sense.

12. The prosthesis or orthosis according to claim 11, wherein said ratio adapting means are such that the conversion ratio is modified to be higher during a relative rotation of said first body and said second body in a first case corresponding to the dorsal flexion phase of a gait cycle, wherein a smallest angle between said extending body parts is decreased, as compared to the conversion ratio during a relative rotation of said first body and said second body in an opposite case corresponding to a plantar flexion phase of a gait cycle, wherein the smallest angle between said extending body parts is increased.

13. The prosthesis or orthosis according to claim 1, wherein said elastic element includes a helical spring.

14. The prosthesis or orthosis according to claim 1, wherein the ratio adapting means consist of a locking or braking mechanism for locking and unlocking one of the first body, second body and third body to one another of said bodies.

* * * * *